US006811989B1

United States Patent
Rabin

(10) Patent No.: US 6,811,989 B1
(45) Date of Patent: Nov. 2, 2004

(54) PANCREATIC ISLET CELL ANTIGENS OBTAINED BY MOLECULAR CLONING

(75) Inventor: Daniel U. Rabin, Branford, CT (US)

(73) Assignee: Bayer Corporation, West Haven, CT (US)

( * ) Notice: Subject to any disclaimer, the term of this patent is extended or adjusted under 35 U.S.C. 154(b) by 0 days.

(21) Appl. No.: 08/468,581

(22) Filed: Jun. 5, 1995

Related U.S. Application Data

(60) Division of application No. 08/239,276, filed on May 5, 1994, now Pat. No. 5,840,836, which is a continuation of application No. 07/872,646, filed on Jun. 8, 1992, now abandoned, which is a continuation of application No. 07/715,181, filed on Jun. 14, 1991, now abandoned, which is a continuation-in-part of application No. 07/441,703, filed on Dec. 4, 1989, now abandoned, which is a continuation-in-part of application No. 07/312,543, filed on Feb. 17, 1989, now abandoned.

(51) Int. Cl.[7] ............... G01N 33/554; G01N 33/564
(52) U.S. Cl. ............... 435/7.24; 435/7.21; 435/7.4; 436/506; 436/519; 436/811
(58) Field of Search ............... 435/7.21, 7.24, 435/7.4; 436/506, 519, 811

(56) References Cited

U.S. PATENT DOCUMENTS 4,751,181 A * 6/1988 Keene ............... 435/69.3
5,200,318 A * 4/1993 Rabin et al. ............... 435/7.21

OTHER PUBLICATIONS

Srikanta et al., Islet Cell Antigens Initial Studies of their Biology and Function, Mol. Biol.Med. 3:113–127, 1986.*
Falk et al., Allele–specific motifs revealed by sequencing of self–peptides eluted from MHC molecules. Nature 351:290, 1991.*
*Joslin's Diabetes Mellitus*, 13th Edition, C. Kahn et al., editors, Lea & Febiger, Philadelphia, 1994, pp. 18–19.
*Diabetes*, Abstract Book, 56th Annual Meeting, Jun. 1996, Abstract Nos. 290,291,293–296,879,882,893,1128,1129 and 1137.
A. Tarkowski et al., *Arthritis and Rheumatism*, 32: 1087 (1989).

N. Seki, *J. Immunology*, 140: 1477 (1988).
D. Trentham, *Science*, 261: 1727 (1993).
J. Courtenay et al., *Nature*, 283: p. 666 only (1980).
C. Verge et al., *Diabetes*, 45: 926 (1996).
I. Durinovic–Bellò et al., *Diabetes*, 45: 795 (1996).
U. Roll et al., *Diabetes*, 45: 967 (1996).
R. Gianani et al., *Diabetes*, 44: 1340 (1995).
M. Myers et al., *Diabetes*, 44: 1290 (1995).
D. Rabin et al., *J. Immunology*, 152: 3183 (1994).
D. Rabin et al., *Diabetes*, 41: 183 (1992).
M. Lan et al., *DNA and Cell Biol.*, 13: 505 (1994).
D. Rabin et al., *J. Immunol. Methods*, 156: 101 (1992).
Abstracts of Medline Search conducted on Jul. 22, 1996.
K. Krisch et al., *Lab. Invest.*, 58: 411 (1988).
M. Solimena et al., *EMBO Journal*, 15: 2102 (1996).
D. Karounos et al., *Diabetes*, 39: 1085 (1990).
D. Karounos et al., *Autoimmunity*, 6: 79 (1990).
C. Goodnow, *Proc.Natl.Acad.Sci. USA*, 93: 2264 (1996).
S. Khare, *J. Immunoology*, 155: p. 3653 only (1995).
B. Driscoll et al., *J. Immunology*, 112: p. 392 only (1974).
M. Samson et al., *J. Immunology*, 155: p. 2737 only (1995).
P. Matsiota et al., *Ann.Inst.Pasteur Immunol.*, 139: 99 (1988), abstract only.
A. Wajgt et al., *Acta Neurol.Scand.*, 68: 337 (1983), abstract only.
D. Daniel et al., *Eur. J. Immunol.*, 25: 1056 (1995), abstract only.
D. Kaufman et al., *Nature*, 366: 69 (1993), abstract only.
R. Tisch et al., *Nature*: 366: 72 (1993), abstract only.
N. Schloot et al., *Immunology Today*, 16: 289 (1995).

* cited by examiner

*Primary Examiner*—Donna C. Wortman
(74) *Attorney, Agent, or Firm*—Norris McLaughlin & Marcus

(57) ABSTRACT

Pancreatic islet cell antigens (ICA) that bind with antibodies found in the sera of patients afflicted with insulin-dependent (Type I) diabetes mellitus (IDDM). ICA proteins are expressed by recombinant cloning vehicles comprising DNA inserts isolated from islet cells. Full sequence native ICA proteins, or protein or peptide fragments thereof, can be used in the diagnosis of IDDM and in detecting or blocking human immunoglobulin, T-cells, or B-cells involved in IDDM.

42 Claims, 14 Drawing Sheets

DIABETIC

NORMAL

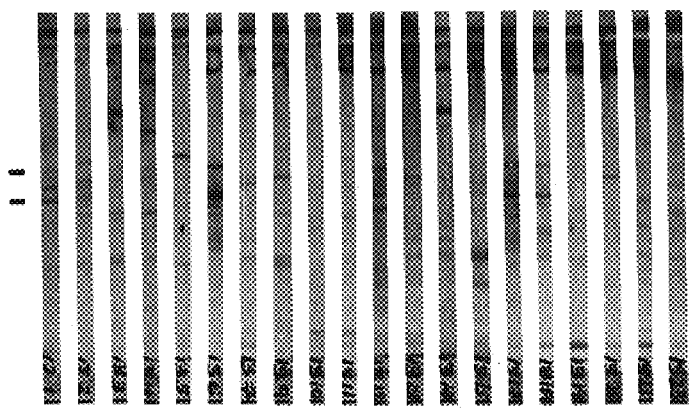 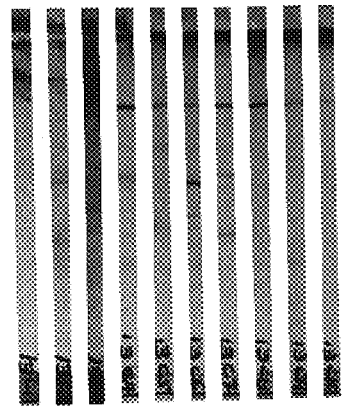
FIG. 2a DIABETIC
FIG. 2b NORMAL

DIABETIC

NORMAL

DIABETIC

NORMAL

DIABETIC

NORMAL

DIABETIC

NORMAL

FIG. 7

| SERUM | | 12 | 13 | 208 | 302 | 313 |
|---|---|---|---|---|---|---|
| 1 | 1 | 3 | 1 | | | 1 |
| 2 | 2 | | | | | |
| 3 | 3 | | | | ? | |
| 4 | 4 | | | | | |
| 5 | 5 | 2 | | 2 | | |
| 6 | 6 | 4 | 2 | 2 | | 3 |
| 7 | 7 | 3 | | 3 | 2 | |
| 8 | 9 | | | 4 | | |
| 9 | 10 | | | | | |
| 10 | 11 | | | | | |
| 11 | 12 | 3 | 2 | | | |
| 12 | 13 | | | | | |
| 13 | 14 | | | 4 | ? | |
| 14 | 15 | | | 3 | | |
| 15 | 17 | 3 | 2 | | | 2 |
| 16 | 18 | 3 | 2 | 1 | | 1 |
| 17 | 19 | ? | | | | |
| 18 | 20 | ? | | | 2 | |
| 19 | 21 | | 1 | 1 | 4 | |
| 20 | 23 | | | | 1 | |
| 21 | c1 | | | | | |
| 22 | c2 | | | | | |
| 23 | c3 | | | | | |
| 24 | c4 | | | | | |
| 25 | c5 | | | | | |
| 26 | c6 | | | | | |
| 27 | c7 | | | | | |
| 28 | c8 | | | 2 | | |
| 29 | c9 | | | | | |
| 30 | c10 | | | | | |

FIG. 8a
FIG. 8b
DIABETIC
NORMAL
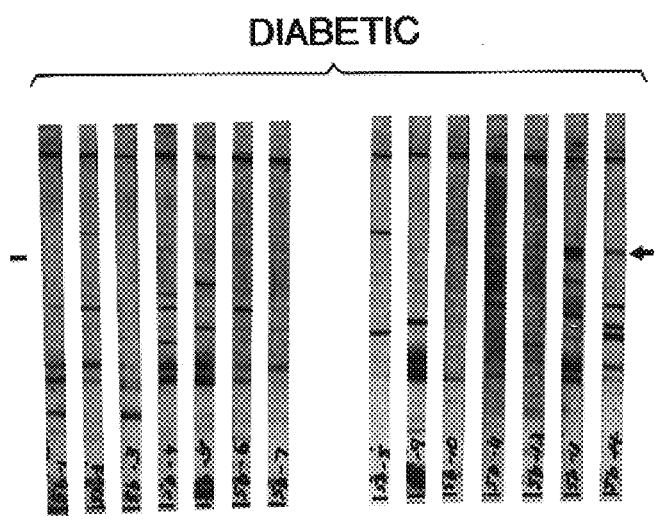
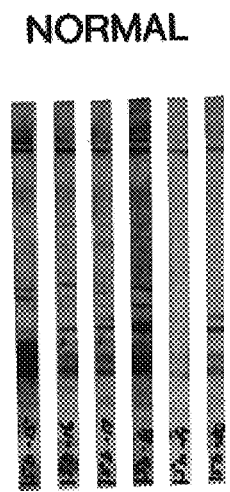

DIABETIC

NORMAL

FIG. 10

PROFILES

| SERUM | | 505 | 525 |
|---|---|---|---|
| 1 | 7601 | | 4 |
| 2 | 7645 | | |
| 3 | 7668 | | |
| 4 | 7677 | | |
| 5 | 13782 | | 4 |
| 6 | 13860 | 1 | 4 |
| 7 | 13916 | | |
| 8 | P5 | | 2 |
| 9 | P6 | 1 | |
| 10 | P7 | | 4 |
| 11 | P8 | | 3 |
| 12 | P21 | | 3 |
| 13 | P26 | 3 | |
| 14 | P28 | 2 | |
| 15 | MRC41 | | |
| 16 | MRC42 | | 1 |
| 17 | MRC43 | 1 | |
| 18 | MRC44 | | |
| 19 | MRC45 | | |
| 20 | MRC46 | | |

PANCREATIC ISLET CELL ANTIGENS OBTAINED BY MOLECULAR CLONING

CROSS-REFERENCE TO RELATED APPLICATION

This application is a divisional of application Ser. No. 08/239,276, filed May 5, 1994, now U.S. Pat. No. 5,840,836, which is, in turn, a continuation of Ser. No. 07/872,646, filed Jun. 8, 1992, now abandoned, which is, in turn, a continuation of Ser. No. 07/715,181, filed Jun. 14, 1991, now abandoned, which is, in turn, a continuation-in-part of Ser. No. 07/441,703, filed Dec. 4, 1989, now abandoned, which is, in turn, a continuation-in-part of Ser. No. 07/312,543, filed Feb. 17, 1989, now abandoned.

BACKGROUND OF THE INVENTION

This invention relates to pancreatic islet cell antigens that bind with antibodies found in the sera of patients afflicted with insulin-dependent (Type I) diabetes mellitus (IDDM). More particularly, the invention relates to proteins and peptides that bind with islet cell antibodies (ICA) and that are prepared by recombinant DNA (rDNA) or synthetic methods. The invention also concerns cloned DNA encoding such ICA proteins and peptides. The ICA proteins and peptides of the present invention are useful as immunoassay reagents in the presymptomatic diagnosis of IDDM.

The accumulating evidence of cellular and humoral abnormalities associated with IDDM has led to the hypothesis that the disease is an autoimmune disorder. Serum antibodies directed against the insulin-producing beta cells of the pancreatic islets have been detected by immunofluorescence, [G. F. Bottazzo, A. Florin-Christensen, and D. Doniach: Islet Cell Antibodies in Diabetes Mellitus With Autoimmune Polyendocrine Deficiencies, Lancet ii:1279–1283 (1974), and A. C. MacCuish, J. Jordan, C. J. Campbell, L. J. P. Duncan, and W. J. Irvine: Antibodies to Islet-cell in Insulin-dependent Diabetics With Coexistent Autoimmune Disease, Lancet ii:1529–1533 (1974)]. These autoantibodies are observed in 70–80% of newly diagnosed diabetics (NDD), but only in 0.1–1% of normal control subjects [C. H. Brogren and A. Lernmark: Islet Cell Antibodies in Diabetes. Clin. Endocrinol. Metab. 11:409–430 (1982)], and G. F. Bottazzo, R. Pujol-Borrell, and D. Doniach: Humoral and Cellular Immunity in Diabetes Mellitus. Clin. Immunol. Allergy 1:139–159 (1981)]. ICAs have come to be accepted as one predictive factor for IDDM. A review of current knowledge on ICA is provided by A. Lernmark, Diabetic Medicine 4:285–292 (1987).

The conventional ICA assay consists of exposing pancreas sections to sera, staining with a second antibody bearing either a fluorescent [G. F. Bottazzo et al., supra] or enzyme label [P. G. Colman, M. Tatkus, A. Rabizadeh, C. Cahill, and G. S. Eisenbarth: Assay for Islet Cell Antibodies with Rat Pancreas and Peroxidase Protein A. Diabetes Care 11:367–368 (1988)], and observing under a microscope. Another similar method involves a biotin-avidin sandwich and immunofluorescent detection [T. Kobayashi, T. Sugimoto, T. Itoh, K. Kosaka, T. Tanaka, S. Suwa, K. Sato and K. Tsuju: The Prevalence of Islet Cell Antibodies in Japanese Insulin-dependent and Non-insulin-dependent Diabetic Patients Studied by Indirect Immunofluorescence and by a New Method. Diabetes 35:335–340 (1986)]. These methods are time consuming, laborious, difficult to reproduce, and have limited sensitivity. The development of a more convenient immunoassay for ICA would permit widespread testing for epidemiology and correlation with IDDM, and ultimately prediction of the disease with a screening test.

A major limitation of current ICA tests is the limited knowledge and characterization of the islet cell antigens involved. The ICA's may be of low titer or affinity and approachable only with characterized antigens. ICA antigens that are detected by the immunofluorescence test are of special interest; these antigens may include:

(1) islet cell surface moieties [N. K. MacLaren, S. W. Hugng, and J. Fogh: Antibody to Cultured Human Insulinoma Cells in Insulin-dependent Diabetes. Lancet 1:997–1000 (1975), and A. Lernmark, Z. R. Freedman, C. Hofmann, A. H. Rubenstein, D. F. Steiner, R. L. Jackson, R. J. Winter and H. S. Traisman: Islet-cell-surface Antibodies in Juvenile Diabetes Mellitus. N. Engl. J. Med. 299:375–380 (1978)], (2) insulin [J. P. Palmer, C. M. Asplin, P. Clemons, K. Lyen, O. Tetpati, P. K. Raghu and T. L. Paquette: Insulin Antibodies in Insulin-dependent Diabetics Before Insulin Treatment. Science 222:1337–1339 (1983), and S. Srikanta, A. T. Ricker, D. K. McCulloch, J. S. Soeldner, G. S. Eisenbarth and J. P. Palmer: Autoimmunity to Insulin, Beta Cell Dysfunction, and Development of Insulin-dependent Diabetes Mellitus. Diabetes 35:139–142 (1986)], (3) a 64,000 dalton (64 kd) islet protein of unknown cellular localization [S. Baekkeskov, J. H. Nielsen, B. Marner, T. Bilde, J. Ludvigsson, and A. Lernmark: Autoantibodies in Newly Diagnosed Diabetic Children Immunoprecipitate Human Pancreatic Islet Cell Proteins. Nature 298:167–169 (1982). Recent evidence indicates that the 64 kd protein is glutamic acid decarboxylase (GAD). [S. Baekkeskov, J-H. Aanstoot, S. Christgau, A. Reetz, M. Solimena, M. Cascalho, F. Folli, H. Richter-Olesen and P. De-Camilli: Identification of the 64k autoantigen in insulin-dependent diabetes as the GABA-synthesizing enzyme glutamic acid decarboxylase. Nature 347:151–156 (1990)], (4) cytoplasmic antigens [G. F. Bottazzo, A. Florin-Christensen, and D. Doniach: Islet Cell Antibodies in Diabetes Mellitus With Autoimmune Polyendocrine Deficiencies. Lancet 2:1279–1283 (1974), A. C. MacCuish, J. Jordan, C. J. Campbell, L. J. P. Duncan, and W. J. Irvine: Antibodies to Islet-Cell in Insulin-Dependent Diabetics With Coexistent Autoimmune Disease. Lancet 2:1529–1533 (1974), R. Lendrum, G. Walker, and D. R. Gambli: Islet-Cell Antibodies in Juvenile Diabetes Mellitus of Recent Onset. Lancet 1:880–883 (1975), and W. J. Irvine, C. J. McCallum, R. S. Gray, G. J. Campbell, L. J. P. Duncan, J. W. Farquhar, H. Vaughan, and P. J. Morris: Pancreatic Islet Cell Antibodies in Diabetes Mellitus Correlated With The Duration and Type of Diabetes, Co-existent Autoimmune Disease, and HLA-type. Diabetes 26:138–147 (1977)], (5) glycoconjugates [R. C. Nayak, M. A. K. Omar, A. Rabizadeh, S. Srikanta, and G. S. Eisenbarth, "Cytoplasmic" Islet Cell Antibodies: Evidence That the Target Antigen is a Sialoglycoconjugate. Diabetes 34:617–619 (1985); P. Vardi, E. E. Dibella, T. J. Pasquarello, and S. Srikanta, Islet Cell Autoantibodies: Pathobiology and Clinical Applications. Diabetes Care 10:645–56 (1987); B. K. Gillard, J. W. Thomas, L. J. Nell and D. M. Marcus, Antibodies Against Ganglioside GT3 in the Sera of Patients with Type I Diabetes Mellitus. Journal of Immunology 142:3826–32 (1989)].

Several reports indicate a high prevalence of anti-64 kd antibody in prediabetic sera as well as newly diagnosed diabetic sera [S. Baekkeskov, M. Landin, J. K. Kristensen, S. Srikanta, G. Jan Bruining, R. Mandrup-Poulsen, C. de Beaufort, J. S. Soeldner, G. Eisenbarth, F. Lindgren, G. Sundquist, and A. Lernmark: Antibodies to a 64,000 MW Human Islet Cell Antigen Precede the Clinical Onset of Insulin-dependent Diabetes. J. Clin. Invest. 79:926–934 (1987), M. A. Atkinson, N. K. Maclaren, W. J. Riley, D. W. Sharp and L. Holmes: Mr 64,000 Autoantibodies (64KA) Predict Insulin Dependent Diabetes. American Diabetes Assoc. 48th Annual Meeting (1988) Abstract #391, and M. A. Atkinson, N. K. Maclaren, D. W. Scharp, P. E. Lacy, and W. J. Riley: 64000 Mr autoantibodies as predictors of insulin-dependent diabetes. The Lancet 335:1357–1360 (1990)].

Some other molecular species have been characterized by Western blotting as being "common antigens" recognized by diabetic sera [D. G. Karounos, V. J. Virta, L. J. Nell, and J. W. Thomas: Analysis of Human and RINm5F Islet Cell Antigens. American Diabetes Assoc. Res. Symp. Woods Hole, Mass. October 1987; Abstract #120]. These antigens have molecular weights of 150 kd, 84 kd, 60 kd, 49 kd, and 36 kd. A more recent report from the same laboratory indicates that there is a RIN antigen of Mr 52,000 that reacts with 29% of diabetic sera. [D. G. Karounos and J. W. Thomas: Recognition of Common Islet Antigen by autoantibodies From NOD Mice and Humans With IDDM. Diabetes 39:1085–1090 (1990), D. G. Karounos, L. J. Nell, and J. W. Thomas: Autoantibodies present at onset of type I diabetes recognize multiple islet cell antigens. Autoimmunity 6:79–91(1990), and D. G. Karounos, J. S. is wolinsky, B. K. Gillard, and J. W. Thomas: Molecular Mimicry in Type I Diabetes: An Antigenic Determinant on a Rubella Virus Protein is Shared with a 52 kD Beta Cell autoantigen. Diabetes 39:96A (1990)]. The first and third references indicate that the 52,000 antigen is RIN specific, not found in human islets or other tissue.

SUMMARY OF THE INVENTION

The present invention provides a series of cloned nucleic acids that code for one or more proteins or protein fragments which bind selectively with pancreatic islet cell antibodies (ICA). Such cloned nucleic acids are characterized by the cDNA inserts in deposited recombinant bacteriophages ATCC 40550, 40551, 40552, 40553, 40554, 40703, 40704, 40705, 40706, and ICA-512.3.

The present invention, accordingly, also provides ICA proteins and peptide fragments thereof which are encoded by the cloned nucleic acids and are useful in the diagnosis of insulin-dependent (Type I) diabetes mellitus (IDDM). The ability of such proteins and peptides to bind to the antibody combining site on ICAs also confers utility in the binding or blocking of human immunoglobulin, T-cells or B-cells involved in IDDM, including circulating immunoglobulin, T-cells, and B-cells.

The ICA proteins and peptides of the present invention are obtained by such methods as full or partial expression, optionally with subsequent fragmentation, of the present cloned nucleic acids; and peptide or polypeptide synthesis based on the amino acid sequences determined from the present cloned cDNAs or from the full length ICA antigen genes that can be determined or isolated from islet cell nucleic acid libraries with the aid of the present complementary cloned cDNA sequences. Accordingly, such ICA proteins and peptides include the full length ICA proteins present in or on islet cells and which are expressed by the human gene whose mRNA is at least in part complementary with the complete sequence of the present cloned cDNAs. Also included in the ICA proteins and peptides of the present invention are the proteins expressed by recombinant cloning vehicles comprising the present cDNA inserts and fragments of such proteins obtained by partial expression or by subsequent fragmentation such as with restriction nucleases. The ICA proteins and peptides of the present invention also include peptides obtained by protein synthesis, such as those that are 3 amino acids in length or longer, which represent ICA epitopes or analogues or derivatives thereof.

The present invention offers a number of significant advantages. The molecular cloning of ICA antigens affords the preparation of large and reproducible amounts of material for use in research, diagnosis, and treatment of IDDM, as well as the opportunity to study the biological mechanisms involved in islet cell destruction and the appearance of ICA. The availability of large quantities of pure antigen enables the development of highly sensitive and specific immunoassays which can be used to screen the general population for presymptomatic IDDM or a predisposition to develop IDDM.

BRIEF DESCRIPTION OF THE DRAWINGS AND SEQUENCE LISTING

FIGS. 1–5, 8 and 9 are reactivity profiles of ATCC-deposited ICA clones prepared in accordance with the present invention with diabetic and normal sera under conditions described in the Examples.

FIGS. 7 and 10 are summaries of the sera profiles of ICA clones showing reactivity values assigned by visual interpretation of the profiles in FIGS. 1–5, respectively.

Figure 1B:
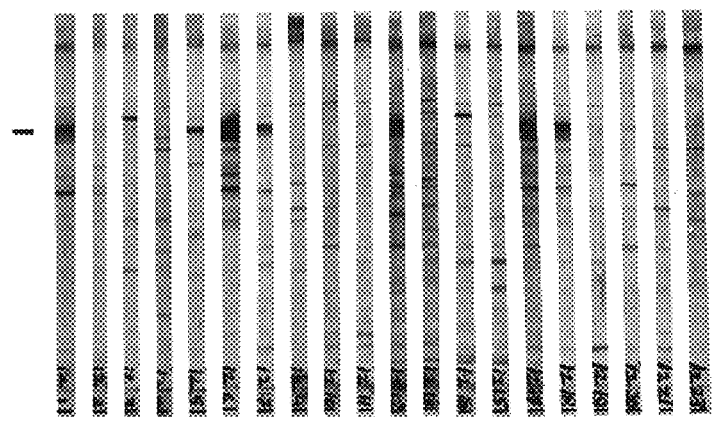
Figure 1A:
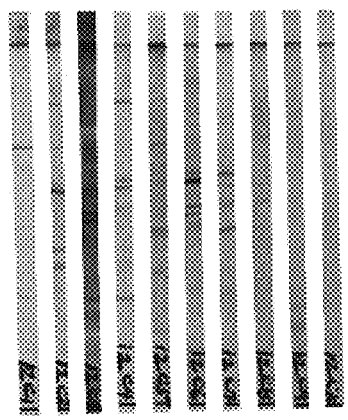
Figure 3A:
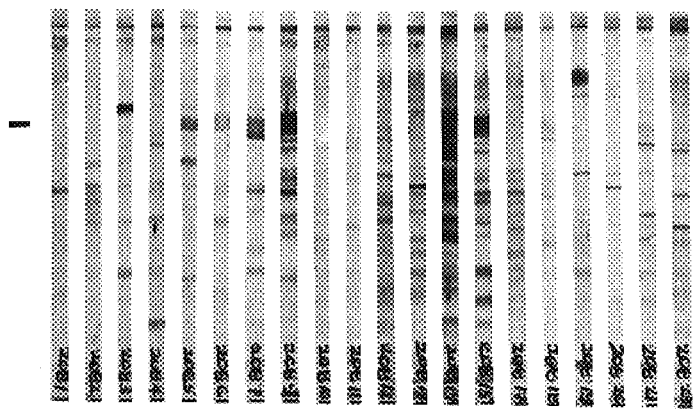
Figure 3B:
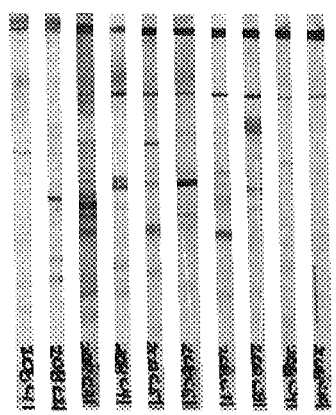
Figure 4A:
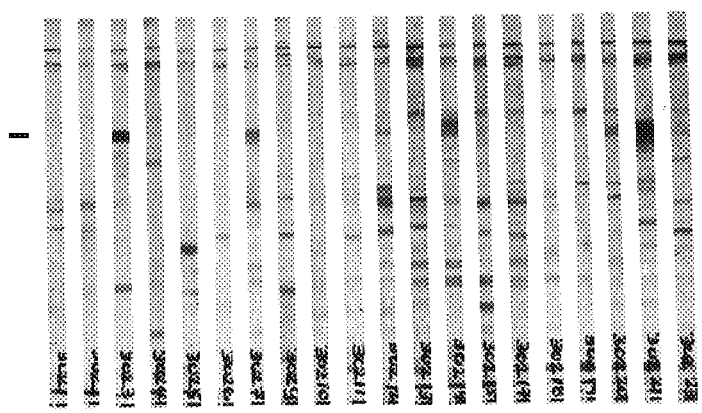
Figure 4B:
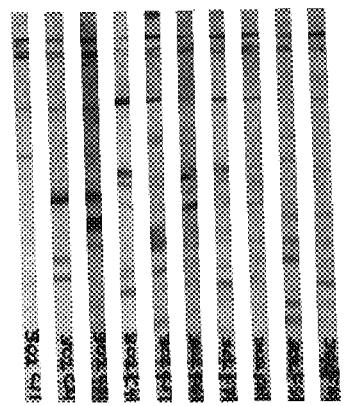
Figure 5A:
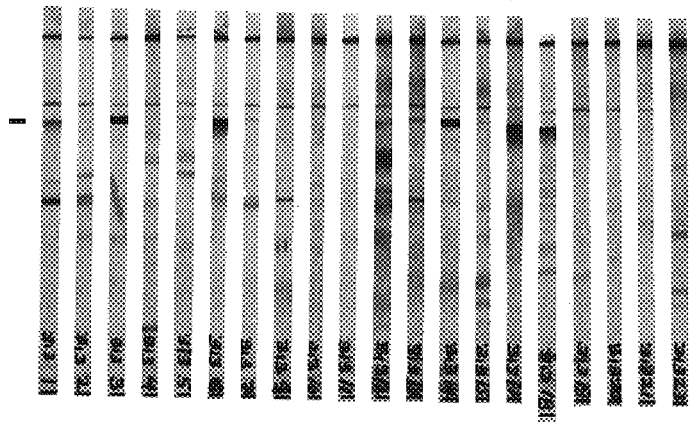
Figure 5B:
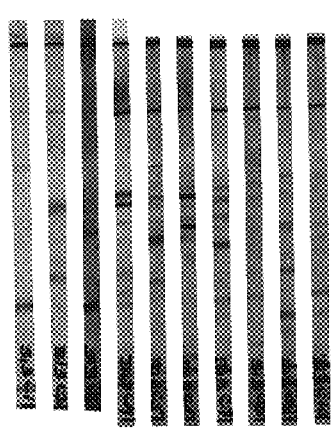

The sequence listing provides the DNA and inferred protein sequences for particular ICA clones as following:

| SEQ ID NO. | ICA CLONE |
| --- | --- |
| 1 | 12 |
| 2 | 13 |
| 3 | 208 |
| 4 | 302 |
| 5 | 313 |
| 6 | 12.3 |
| 7 | 525 |
| 8 | 505 |
| 9 | 512 |
| 10 | 512.3 |

DESCRIPTION OF THE PREFERRED EMBODIMENTS

As used herein, the term "ICA antigens" shall be understood to refer to the proteins and peptides provided by the present invention even though it is recognized that in some cases peptide forms will not be "antigens" in the strict sense, i.e., they will be haptenic since they will require attachment to a conventional macromolecular carrier in order to stimulate the production of antibodies in a host animal.

Furthermore, the "cloned nucleic acids", "cloned ICA antigen sequences", "cDNA inserts", and like terms shall refer to the inserts in deposited recombinant phages ATCC 40550, 40551, 40552, 40553, 40554, 40703, 40704, 40705, 40706, and ICA-512.3, and also to other nucleic acid sequences of full length genes, or fragments of such sequences, comprising such deposited sequences. It will be recognized that one or more full length ICA antigens are characterized by homology with the above deposited cDNA inserts, however, it is possible that two or more of such cDNA inserts correspond to a single ICA antigen. For example, the insert in ATCC 40703 appears to encompass the inserts for both ATCC 40550 and ATCC 40554, and thus these three inserts may all correspond to different and/or overlapping portions of a single ICA antigen. Moreover, ATCC 40706 is comprised in ICA-512.3.

Preparation of Cloned ICA Antigen Sequences

In general, the cloned ICA antigen sequences is of the present invention are obtained by expressing human genes in a suitable recombinant cloning vehicle, e.g., bacteriophage, and probing the resulting gene library with IDDM serum to select antigens that are recognized by ICA antibodies. Recombinant antigens are then screened with a panel of diabetic and normal sera to determine the disease specificity of the identified clones.

The particular deposited clones were more particularly obtained by the following method (further details can be found in the Examples below). A human cDNA library was generated by extracting RNA from purified human islets. This RNA was fractionated by chromatography to separate poly-A mRNA from other RNA such as ribosomal RNA and fragments of degraded RNA. The separated mRNA was reverse transcribed with a commercially available cDNA kit (Bethesda Research Laboratories), ligated to Eco RI DNA linkers, and ligated into lambda gt-11 arms for in vitro packaging. The ligated lambda was packaged using a commercial kit (Stratagene) and then amplified on a bacterial lawn in a plate format.

The phage library was screened with antibodies from autoimmune patients with Type I diabetes. Agarose plates were spread with bacteria infected with the phage, and recombinant protein expression was induced chemically. The protein was deposited onto filters which were then probed with serum. Plaques that appeared to be positive were isolated from the agarose plates and purified through two rounds of isolation. Subsequent to cloning, the gt-11 phage was infected into a bacterial host for large scale expression. Specificity of the proteins expressed by the cloned cDNA was evaluated by Western blotting of bacterial extracts containing the cloned human protein. Preparative polyacrylamide gels were run and electroblotted onto membranes, the membranes were cut into strips, and then reacted with a series of normal and diabetic sera. The clones that generated proteins that reacted exclusively or predominantly with diabetic sera were selected.

Recombinant Cloning Vehicles and Subcloning

As is conventionally known in the art, the cDNA transcripts of the present invention, such as library cDNA or cDNA inserts excised from a cloning vehicle, can be incorporated into a variety of recombinant cloning vehicles for amplification of sequences of interest and for expression of ICA antigens of interest. A recombinant cloning vehicle will be understood to be a biochemical molecule or structure, e.g., DNA, that allows insertion of polynucleotide sequences and replication of the inserted polynucleotide sequences when the vehicle is appropriately incorporated into a host cell. An expression vehicle additionally includes the property of expressing the protein encoded by the inserted polynucleotide. In an expression vector, the inserted ICA antigen sequence is operably linked to a suitable control sequence capable of effecting the expression of ICA antigen in a suitable host. The control sequence involved will vary according to the host and transformation method selected. These matters are within the ordinary skill of the art.

Suitable recombinant cloning vehicles include plasmids, viruses and bacteriophage, and integratable fragments of DNA (i.e., fragments integratable into the host genome by recombination). Expression vehicles are particularly preferred and are exemplified, without limitation, by bacterial pEMBL, pMMB, pUK, pATH, and pGEX, yeast pAAH5, pYE4, and pAB112, mammalian pRSV, vaccinia derived vectors, baculovirus derived vectors, papilloma derived vectors, retroviral vectors, and shuttle vectors such as pCDM8. For a review, see D. M. Glover, DNA Cloning: A Practical Approach (1985) IRL Press Ltd. Suitable host cells include procaryotes, yeast, and higher eucaryotic cells including mammalian cells.

Subcloning of cDNA inserts can involve excising the insert for ligation into a different cloning vehicle. The insert can be excised using the restriction enzyme corresponding to the linkers used in the original insertion or using restriction enzymes selected from a restriction map of the insert. The excised cDNA can be inserted into another suitable vector for sequencing, amplification, or expression as desired. Should the terminal restriction sites in the original cloning vehicle have been destroyed, other enzymes can be used to recover the insert and resulting flanking regions from the cloning vehicle deleted by conventional means.

Another method of preparing DNA fragments for insertion into a cloning vehicle is the use of polymerase chain reaction (PCR) amplification. This procedure can be used on ligation reaction products to amplify the amount of DNA and introduce desired restriction sites for subcloning. PCR can also be used to replicate a fragment with desired restriction sites for transfer from one vehicle into another vehicle.

Full-Length Gene Cloning

Fragments of the cDNA inserts of the present invention can be used to isolate full-length cDNA or genomic DNA clones from appropriate libraries by standard methods. The target library is spread on plates, allowed to grow, transferred to filters, and reacted with DNA probes. Such DNA probes are generated from restriction fragments of the cDNA inserts by such methods as end labeling, nick translation, random primed transcription, or photochemical means. Oligonucleotides can be synthesized, labeled, and used as hybridization probes. RNA probes can also be generated from subcloned cDNA by transcription from appropriate templates.

Recombinant cloning vehicles, e.g., phage or plasmids, that appear to react with the partial cDNA clones are re-screened and then restriction mapped. Promising clones are then sequenced to confirm the hybridization of the original probes and to obtain extended sequence information on the larger fragment. If full-length clones are not obtained in this procedure, the complete sequence of the nucleic acid coding for the human gene can be pieced together from overlapping sequences of cloned fragments.

An alternative method for obtaining longer fragments, and possibly full-length clones, uses antibodies raised against ICA antigens expressed by partial clones. After identifying an antigen of interest, it can be used as an immunogen to raise monoclonal or polyclonal antibodies of high titer and affinity. Such antibodies will enable the detection of longer cDNA clones and cDNA clones present in lower amounts in the library.

Antigen and Peptide Synthesis

ICA antigens, as defined herein, can be prepared in a number of different ways from the clones and sequence information provided by the present invention. One can simply express the proteins from ICA antigen clones obtained according to the present invention, particularly from the deposited clones. Such expressed proteins, or fragments or digestion products thereof, can be used as antigens for binding to islet cell antibodies. However, direct use of bacterial expression extracts may not be possible in some cases since human sera normally react nonspecifically with *E. coli* proteins. In such cases, the expressed ICA antigens can be isolated by conventional techniques such as electrophoretic separation followed by immobilization on membranes (Western blotting), or by column chromatography or affinity purification (e.g., anti-beta-galactosidase affinity resin chromatography or other conventional biochemical means, e.g., salt or temperature precipitation).

Alternatively, peptide fragments can be synthesized by well-known methods from the amino acid sequences deduced from experimentally determined DNA sequences of ICA antigen clones. Overlapping peptides can be synthesized and tested for reactivity with ICA sera. As reactive peptides are found, smaller peptides can be prepared in order to map the smallest reacting unit, i.e., the epitope.

Methods

A principal use of the ICA antigens provided by the present invention is in the diagnosis and prediction of IDDM. In such a method, a blood sample, normally a serum sample, is reacted with a selected one or series of ICA antigens and immunoreactivity determined by any conventional technique. It is further contemplated that the immunoreactivity profile with different ICA antigens can provide diagnostically significant information concerning the nature of the disease, e.g., subtypes, the state of the disease, the proximity to onset of the disease, the efficacy of therapy, e.g., immune therapy, and the like.

A further use of the present ICA antigens is in the identification, marking, or specific destruction of autoreactive B-cells. If autoantibodies have a deleterious effect in IDDM, it is contemplated that anti-B-cell therapy can slow or stem the progress of the disease from prediabetes to clinical IDDM.

Another use of the present ICA antigens is in the identification of islet-reactive T-cell populations. ICA antigens can serve as stimulating antigens for T-cell culture, permitting significantly improved T-cell cloning, identification, and growth. It is contemplated that ICA T-cell detection can be significant in the diagnosis of the pre-diabetic state, and that monitoring the level of autoreactive T-cells can give an indication of the progress of the disease and the utility of immune modulating therapies. Further, the generation of ICA T-cell cultures can provide an in vitro model for designing diabetic therapies. Finally, it is contemplated that T-cell immunization can halt or retard autoimmunity by generating a humoral response against self-destructive elements.

The ability of ICA antigens to bind to human ICA immunoglobulin and T-cells can be used to block the binding of ICA to islet cells and islet cell components in vivo, and therefore are contemplated to provide a direct therapeutic effect.

The present invention will now be illustrated, but is not intended to be limited, by the following examples.

EXAMPLES 1. cDNA Library

Islets of Langerhans were purified by Dr.'s Paul Lacy and David Scharp at Washington Univ., St. Louis, Mo., USA, following a published procedure. [C. Ricordi, P. E. Lacy, E. H. Finke, B. J. Olack, and D. W. Scharp: An Automated Method for Isolation of Human Pancreatic Islets. Diabetes 37:413–420 (1988)]. Briefly, human pancreas was perfused with collagenase and then ground up. Ficoll gradient centrifugation was used to isolate the islets, which were then cultured for 1 week at room temperature. The islets were frozen and shipped.

Upon receipt, the islets were thawed, pooled, and washed. RNA was extracted using guanidinium thiocyanate and selectively precipitated with lithium chloride [G. Cathala, J. F. Savouret, B. Mendez, B. L. West, M. Karin, J. A. Martial, and J. D. Baxter: A Method for Isolation of Intact, Transtationally Active Ribonucleic Acid. DNA 2:329–335 (1983)]. About 770 $\mu$g of total RNA was obtained from each ml of centrifuged islets. Messenger RNA was purified using Pharmacia Oligo(dT)-cellulose Type 7 (Pharmacia Fine Chemicals, Piscataway, N.J., USA), following the procedure of Maniatis et al, [T. Maniatis, E. F. Fritsel, and J. Sambrook: Molecular Cloning, A Laboratory Manual (1982) Cold Spring Harbor Laboratory p. 197–198]. About 30 $\mu$g RNA was obtained after chromatography. In vitro translation using a BRL kit #8110 (Bethesda Research Laboratory, Gaithersburg, Md., USA), and $^{35}$S-methionine showed a broad range of molecular weight proteins being produced.

A BRL #8267SA kit was used for cDNA synthesis. Ten (10) $\mu$g of poly-A$^+$ RNA was used in the reaction. The ends were polished with T$_4$-DNA polymerase (Pharmacia), and the cDNA was methylated with Eco RI methylase (New England Biolabs, Beverly, Mass., USA) and S-adenosyl methionine and ligated to Eco RI linkers. The cDNA was digested with Eco RI and run on a Biogel A15M column (BioRad Laboratories, Rockville Center, N.Y., USA) to separate the linkers and fragments.

The cDNA was ligated into lambda gt-11 arms and packaged with a Stratagene Gigapack Plus kit (Stratagene Cloning Systems, LaJolla, Calif., USA). A library of approximately 8.5×10$^5$ insert-containing clones was obtained (measured with 5-bromo-4-chloro-3-indolyl-$\beta$-D-galactopyranoside), and amplified on *E. coli* Y1090 (Stratagene).

2. Sera

Sera from newly diagnosed diabetics were obtained from Dr. William Riley at the University of Florida, Gainesville, Fla., USA, and Dr. Alan Drash at the Children's Hospital of Pittsburgh, Pittsburgh, Pa., USA. Normal (non-diabetic) sera were collected from individuals in the laboratory. Sera from non-diabetic children were obtained from Dr. Jocelyn Hicks at the Children's National Medical Center in Washington, D.C. Sera were multiply adsorbed with filters that were prepared either by (a) lysing lambda-infected *E. coli* with chloroform and soaking nitrocellulose filters in this lysate, or (b) preparing filters by overlaying filters soaked with isopropyl-$\beta$-thio-galactopyranoside (IPTG) on lambda-infected *E. coli* in a plate format, essentially in the same manner as screening the library. Sera were diluted 1/20–1/200 in blotto solution (5% Carnation non-fat dry milk, 10 mM Tris pH 8.0, 150 mM NaCl, 0.05% Tween-20, and 0.05% sodium azide) after crude fractionation as noted below. Sera were used for ELISA experiments without preadsorption.

3. Screening

The screening procedure is based on standard protocols (T. V. Huynh, R. A. Young and R. W. Davis: Constructing and Screening cDNA Libraries in Fgt 10 and Gft 11 in DNA Cloning. D. M. Glover ed. (1985) IRL Press p. 490–78). Filters were prepared by plating about 50,000 plaque forming units (pfu) of the library onto each of ten 150 mm agarose plates. After growth at 42° C. for about 3 hours, filters (Nitrocellulose from Schleicher and Schuell, Keene, N.H., USA) containing IPTG were laid onto the plates and growth was continued at 37° C. for either 3–4 hours or overnight. Filters were blocked with a blotto solution and stored at 4° C.

Initially, all antibody reactions with filters were performed at room temperature for 3 hours. In later experiments, sera incubations were done overnight at 4° C. in blotto solution without Tween-20, while secondary antibody reactions were done at room temperature for 1.5 hours. All incubations and washing were done on platform shakers with gentle rotation.

The library was screened with human antibody probes several times. In the first instance, antibody was purified from diabetic sera by HPLC. In the second and third, sera were precipitated with 50% ammonium sulfate and dialyzed. For the first and third screenings, a mixture of two sera were used for all rounds of purification. For the second screening, a mixture of 20 diabetic sera was used for the primary purifications. In a further screening, 22 sera were pooled, precipitated with ammonium sulfate and dialyzed, and the final working dilution of each serum was 1/500 in blotto without Tween 20.

After incubation in the diabetic sera, filters were washed 5–10 minutes each in Tris-buffered saline (TBS), TBS with 0.05% Tween-20, and then in TBS. Human antibody bound to the filters was detected by reaction with rabbit anti-human IgG conjugated to alkaline phosphatase (1/500 in blotto, Dakopatts antibody D-336—DAKO Corp., Santa Barbara, Calif., USA). Filters were washed in TBS/Tween-20, TBS, TBS, and then detection buffer (0.1 M Tris-HCl, pH 9.5, 0.1 M NaCl, 0.05 M $MgCl_2$, recommended by BRL for use in their DNA detection kit No. 8239SA). Chromogenic substrates (nitro-blue tetrazolium and 5-bromo-4-chloro-3-indoyl phosphate) were added and the reaction was protected from light. After color development, the filters were washed in water, then in 10 mM Tris (pH 8.0), 1 mM EDTA (TE) and dried. Best observation of the plaques could be made when the filters were still matte wet.

Positive plaques were located on the original plates by alignment with the filters. For primary screens, a plug containing a positive plaque was removed using the butt end of a sterile Pasteur pipet. For subsequent screenings where individual plaques could be distinguished, the tip of the pipet was used. Plaques were eluted into plaque storage buffer (Maniatis et al., supra) and eluted for at least several hours.

The above screening methods produced the specific deposited ICA clones described herein with the exception of ICA-12.3 and ICA-512.3 which were isolated as follows.

Approximately $10^6$ plaque forming units of the phage library were screened by DNA hybridization for the presence of sequences homologous with the ICA-12 cDNA. The phage plaques distributed over 20 agar plates were replicated onto nylon filters, and the phage DNA was denatured and immobilized for hybridization, by the conventional procedure of Benton and Davis (1977) Science 196:180. The hybridization probe was an agarose gel-purified sample of the cloned ICA-12 cDNA separated from its plasmid vector by Eco RI digestion. The cDNA segment was tagged with $^{32}P$ by the random primer labeling method (Feinberg and Vogelstein (1984) Anal. Biochem. 137:266). Hybridization of the probe to nylon filters was done according to Berent et al. (1985) BioTech. 3:208. Phage plaques identified as containing DNA homologous with the ICA-12 probe were picked from the master plates, and the phage were replicated for a second round of hybridization screening. Individual plaques remaining positive for ICA-12 sequences were then characterized as to properties of cDNA inserts. The clone ICA-12.3 was found by DNA sequence analysis to contain the entire protein coding sequence of the mRNA partially represented in ICA-12.

Monoclonal antibodies (mAb) were raised using GST-ICA-512 (see below) as immunogen. A mixture of culture supernatants from three mAb clones were pooled and used to screen the human islet lambda-gt11 expression library. The screening method was as described above, except that an alkaline phosphatase conjugated rabbit anti-mouse Ig (DAKO) was used as a second antibody. Clone ICA-512.2 was obtained and determined to have 670 bases more than ICA-512 on the 5' end.

Since it appeared that ICA-512.2 did not contain the initiation site for the full length protein, a DNA probe was made by labelling a 230 base Pst I restriction fragment that was derived from the 5' section of ICA-512.2, (bases 201–431, corresponding to bases 1216–1446 of ICA-512.3, shown in SEQ ID NO 10). This fragment was used to screen the library, and clone ICA-512.3 was identified. SEQ ID NO 10 shows the DNA and inferred protein sequence of this clone.

4. Expression

The proteins expressed by individual clones were analyzed by expressing the clones in *E. coli* hosts. Initial expressions with clones identified as ICA-12 and ICA-13 were done with lysogens generated with the clones by standard means (Huynh, et al.). Subsequent expressions were done by infective expression into *E. coli* CAG-456 [M. Snyder, S. Elledge, D. Sweetser, R. A. Young, and R. W. Davis: Fgt-11: Gene Isolation with Antibody Probes and Other Applications, Meth. Enzymology 154:107–128 (1987)]. Cells were harvested and lysed by resuspension in Laemmli sample buffer [U. K. Laemmli, Nature 227:680 (1970)]. Better electrophoresis results were obtained when samples were sonicated to reduce the size of the DNA and reduce viscosity.

Protein gel electrophoresis and semi-dry electrotransfer onto either nitrocellulose (Schleicher and Shuell) or Immobilon (Millipore Company, Bedford, Mass., USA) were performed. Gels were stained with Coomassie Blue and filters were detected by immunoreaction with the same sera used to screen the library as detailed above.

5. Clone Analysis

In order to assess the usefulness of the individual clones for diagnosis of IDDM, each clone was tested for reactivity with a panel of diabetic and normal sera. This was done by reacting each serum with a Western blot strip from each clone. Preparative gel electrophoresis was followed by semi-dry electrotransfer of the proteins to filters. Identical 3 mm strips were cut from the filters and exposed to the various sera. Localization of antigen bands was done by reference to analytical Western blots and strips reacted with anti-beta-galactosidase antibody (1/2000 monoclonal antibody from Promega, Madison, Wis., USA). Antibody incubation and detection with secondary antibody were described above.

Figure 6A:
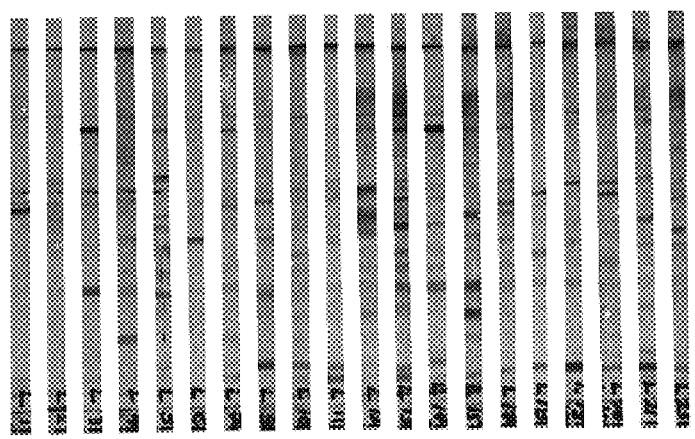
FIG. 6 is a control profile using the cloning phage with no recombinant insert.
Figure 6B:
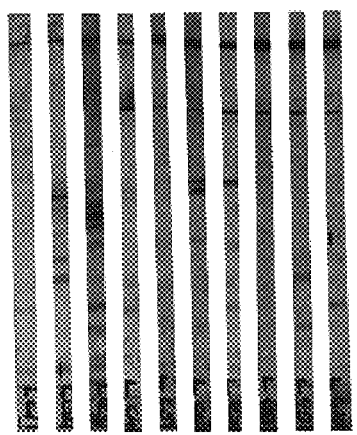
Figure 9A:
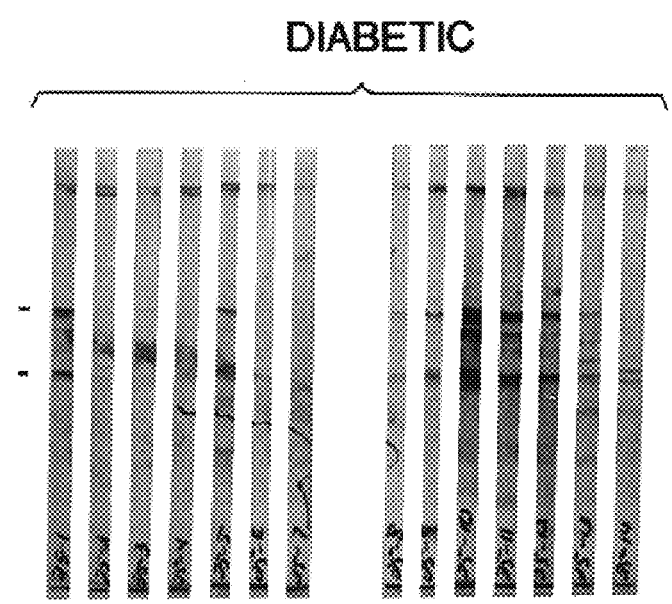
Figure 9B:
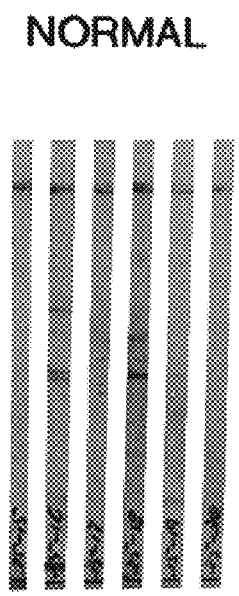
Figure 11A:
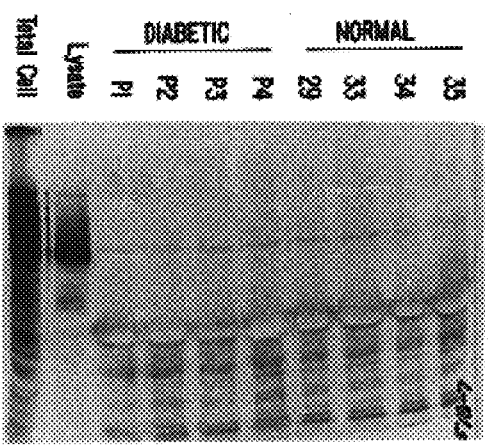
FIG. 11 shows the results of immuno-precipitation of one of the ICA clones with diabetic and normal sera.
Figure 11B:
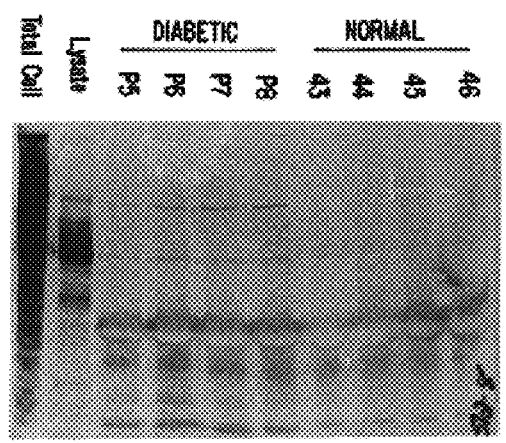
Figure 11C:
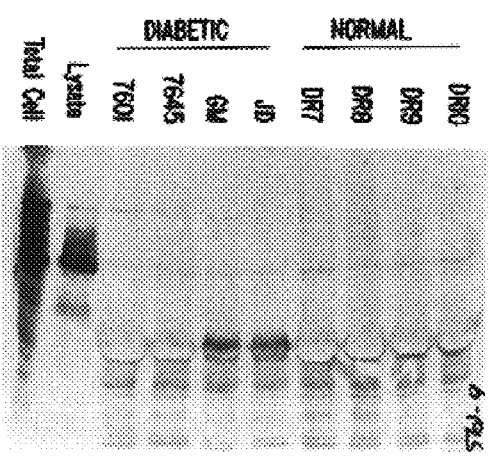
Figure 11D:
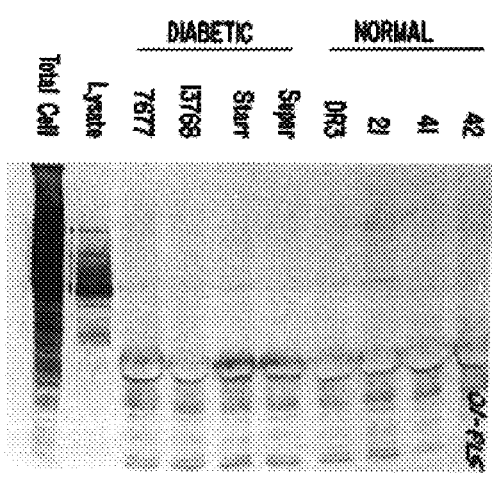

The reactivity profiles of the clones identified as ICA-12, ICA-13, ICA-208, ICA-302, ICA-313, ICA-505, and ICA-525 are shown in FIGS. 1–5, 8 and 9 of the drawings. Identical filter strips were cut from preparative electrotransfer is and reacted with diabetic and normal sera (for ICA-12, 13, 208, 302, and 313, the strips were reacted with 20 diabetic and 10 normal sera; while 14 diabetic and 6 normal sera were used for ICA-505 and 525). A control profile using the vector (lambda gt-11) having no DNA insert is shown in FIG. 6.

The filter strips were also rated according to intensity, 1=weak reactivity, 2, 3 and 4=very strong reactivity. Summaries of the reactivity ratings are given in FIGS. 7 and 10 of the drawings. In FIG. 7, sera 21–30 bearing the prefix "c" are the normal control sera, while the diabetic sera are presented with their source identification number. In FIG. 10, sera 15–20 bearing the "MRC" prefix are normal control sera, while again the diabetic sera are presented with their source identification numbers. In both Figures, the numbers shown under the clone headings represent the strength of immunoreactivity assigned by visual interpretation.

Some clones identified in the first screening were found to be unreactive in the Western blot format. To test the serum reactivity of these clones, the lambda gt-11 phage were expressed in *E. coli* CAG456 as above and the antigen was extracted by treating the bacteria with 4 mg/ml lysozyme (Sigma, St. Louis, Mo., USA) in 25 mM Tris, pH 8, 10 mM EDTA, 50 mM glucose and 2 mM phenyl-methyl sulfonyl chloride (PMSF) for 5 minutes at room temperature. Cells were pelleted at 4° C. and resuspended in ice cold buffer (500 mM sodium chloride, 1% NP-40, 50 mM Tris, pH 8, 1 mg/ml aprotinin (Sigma), 2 mM PMSF, 2 µg/ml chymostatin (Sigma), 2 µg/ml Antipain (Sigma) and 2 µg/ml pepstatin. Extraction of antigen proceeded for 30 minutes on ice, during which time the solution was sonicated. Samples were spun in an Eppendorf microfuge for 5 minutes at 4° C. and supernatants were used for immunoprecipitation.

Immune reactions consisted of: 15 µl wash buffer (50 mM Tris, 150 mM sodium chloride, 1% NP-40, 5 mM EDTA, 2 mM PMSF, 2.5 µl human serum, and 10 µl extract. Reactions were left overnight. Antigen-antibody complexes were recovered with 20 µl of a 50% slurry of Protein-A Sepharose CL-4B (Pharmacia) for 1 hour on ice. The resin was washed six times with 500 µl of wash buffer and once with water. Sample buffer for PAGE was added and the samples were boiled for 5 minutes, centrifuged for 5 minutes, and run on 8% gels. Electroblotting was performed and the blots reacted with anti-beta-galactosidase antibody (1/1000 dilution of Sigma #G4644 in blotto solution) followed by anti-mouse Ig coupled to alkaline phosphatase (DAKO #D314) and development in dyes. The results are shown in FIG. 11 for an extract of ICA-512. Arrows indicate the position of the recombinant antigen.

DNA insert size for the various clones was determined by growing them either in a plate lysate or liquid lysate format (Maniatis, et al., supra). Lambda DNA was extracted, and cut with Eco RI, and analyzed for size by agarose gel electrophoresis.

The above identified clones which reacted predominantly with diabetic sera have been deposited with the American Type Culture Collection, Rockville, MD., USA. The SEQ ID NOs, deposit numbers, deposit dates, and determined insert sizes are shown in Table 1 below. All restrictions upon public access to these deposits will be irrevocably removed upon the grant of a patent and each deposit will be replaced if viable samples cannot be dispensed by the depository.

TABLE 1

| SEQ ID NO | Clone # | ATCC # | Deposit Date | Insert size (kb) |
|---|---|---|---|---|
| 1 | ICA-12 | 40550 | Feb. 8, 1989 | 1.400 |
| 2 | ICA-13 | 40553 | Feb. 8, 1989 | 5.043 |
| 3 | ICA-208 | 40554 | Feb. 8, 1989 | 0.575 |
| 4 | ICA-302 | 30551 | Feb. 8, 1989 | 0.794 |
| 5 | ICA-313 | 40552 | Feb. 8, 1989 | 2.391 |
| 6 | ICA-12.3 | 40703 | Nov. 14, 1989 | 3.243 |
| 7 | ICA-525 | 40704 | Nov. 14, 1989 | 3.4 |
| 8 | ICA-505 | 40705 | Nov. 14, 1989 | 0.346 |
| 9 | ICA-512 | 40706 | Nov. 14, 1989 | 1.8 |
| 10 | ICA-512.3 | 75030 | June 13, 1991 | 3.3 |

DNA inserts were transferred to a Stratagene Blue-script vector. Sequencing was done by standard techniques using the T7 Sequencing kit (Pharmacia) in conjunction with the Stratagene Exo III/Mung bean nuclease kit for generating overlapping nested deletion series of plasmids.

The sequence is considered to be complete for ICA-12, 302, 313, 208, 505, 12.3, 512, and 512.3, while only partial sequencing is available for ICA-13 and 525. The DNA sequences are those experimentally derived as described above. All three possible reading frames in both orientations were examined for protein coding capability, i.e., long open read frames. The most likely protein sequence for each clone is presented in capital letters below the DNA sequence (except for ICA-505 for which the available information does not permit assignment of the reading frame encoding the protein antigen).

ICA-512 was transferred to a modified version of plasmid pGEX (Pharmacia) for protein expression and purification. This modified plasmid, pGEXc, was adapted for expression of lambda-gt11 products by inserting 2 additional bases between the Bam H1 and EcoRI restriction sites.

A pGEXc clone that was determined to bear the ICA-512 insert in the correct orientation by restriction analysis and DNA sequenceing was expressed following the protocol suggested by the manufacturer (Pharmacia) except that growth after induction with IPTG was at 25° C. Cell lysis, purification of the GST-ICA-512 fusion protein on a glutathione-Sepharose 4B column, cleavage of the fusion protein with thrombin (Sigma T-7009) and purification of the ICA-512 cleaved product with glutathione-Sepharose 4B were performed as described [D. B. Smith and K. S. Johnson: Single-step purification of polypeptides expressed in *Escherichia coli* as fusions with glutathione S-transferase. Gene 67:31–40 (1988)].

ICA-512 was adapted to an ELISA format to provide quantitative information about a large number of samples. Both the GST-ICA-512 and the cleaved ICA-512 were evaluated, and shown to give similar results with a panel of normal and diabetic sera.

Figure 12:
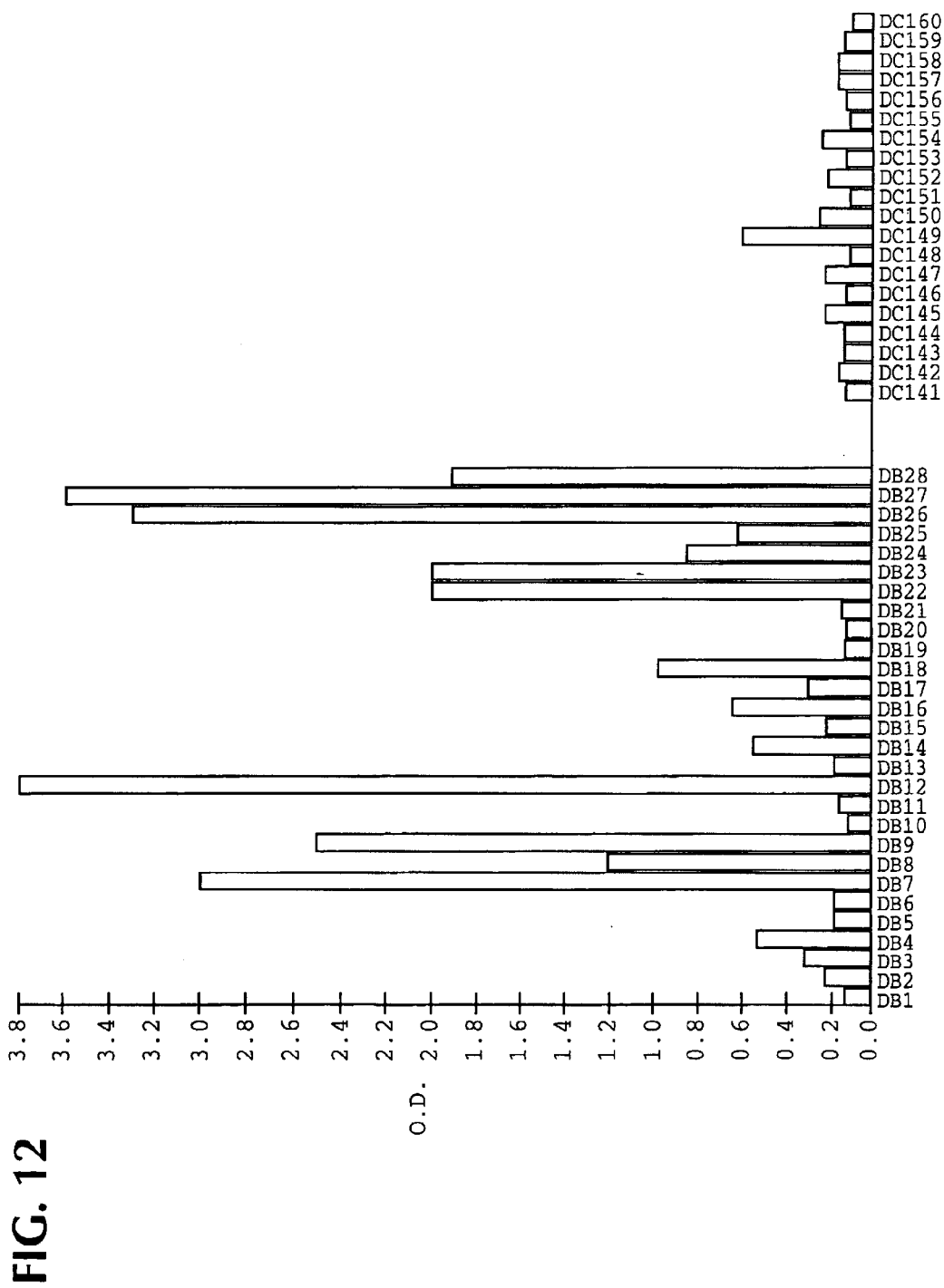
FIGS. 12 and 13 show ELISA profiles illustrating the specificity of reactivity of particular ICA clones (ICA-512 and ICA-12) with diabetic sera.

FIG. 12 shows the reactivity of ICA-512 with such a panel. The "DB" sera on the left are newly diagnosed diabetics, and the "DC" sera on the right are normal sera. In this experiment, 30 ng of cleaved and purified ICA-512 was deposited in each well of an Immulon-2 microtiter plate (Dynatech, Chantilly, Va.) in TBS buffer and allowed to stand overnight. Other coating buffers have been tested and shown to be equivalent. All incubations and reactions were done at room temperature with orbital shaking. Unbound antigen was shaken out. The plate was blocked with a blotto solution containing Tween-20 for 1 hour, and then reacted with 1.5 µl of human serum diluted in 50 µl blotto/Tween. Incubation was for 1 hour. After washing 5 times with PBS/Tween, the wells were incubated with 100 µl of a 1/000 dilution of alkaline phosphatase (AP) conjugated anti-human IgG antibody (Sigma A-0287) for 1 hour. After washing 5 times in PBS/Tween and once for 15 minutes with TBS/Tween, the plate was developed with nitrophenyl-phosphate (1 Sigma tablet #104-105 in 10 μl of 1 M diethanolamine, 0.5 mM MgCl$_2$, pH 9.8) for 1–2 hours. Optical density was read at 405 nm.

Figure 13A:
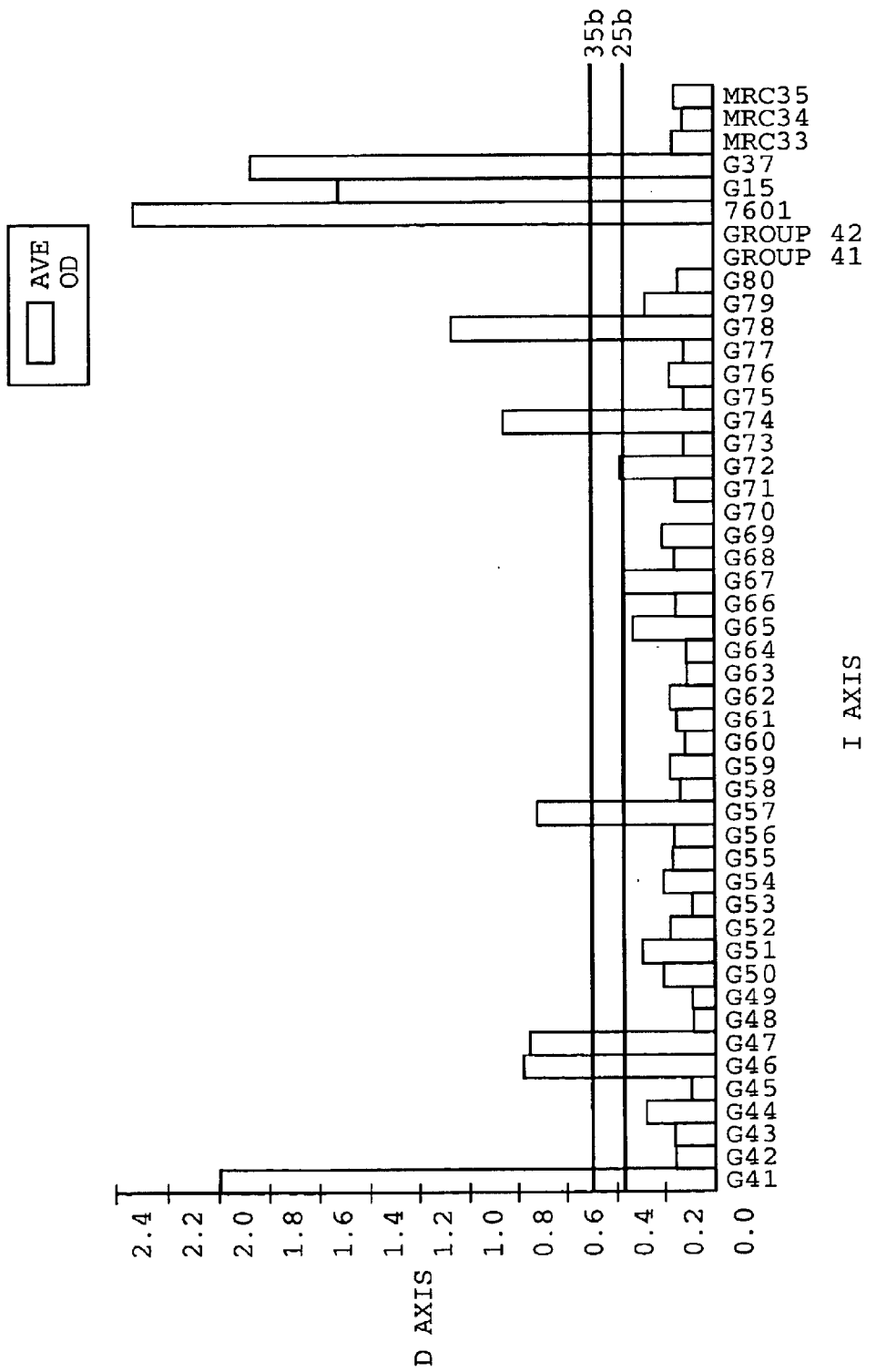
Figure 13B:
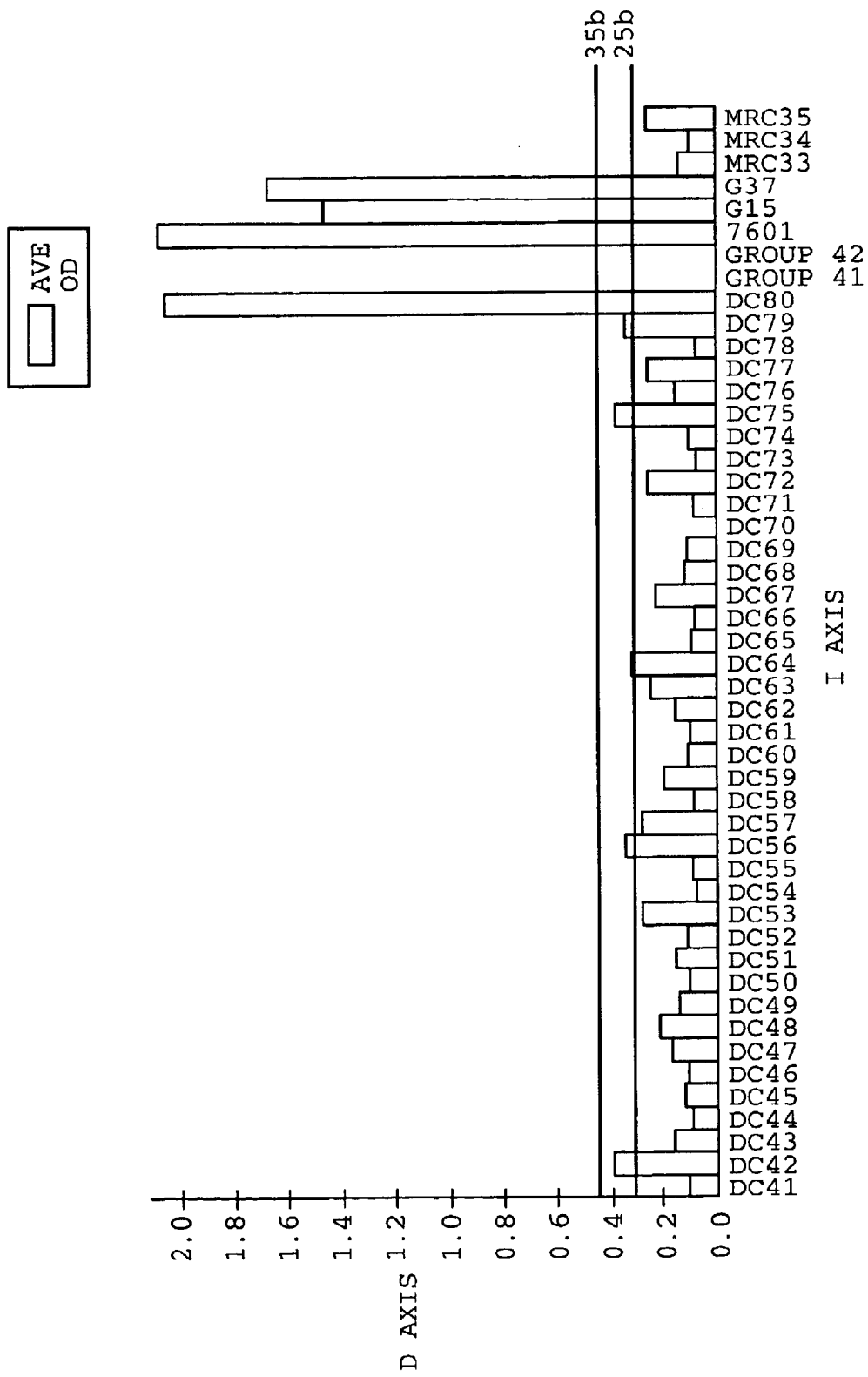

FIG. 13 shows the reactivity of a panel of diabetic (G) and normal (DC) sera with ICA-12 in an ELISA format. The last 6 sera on the right side of the panel are controls. In this experiment, a capture format was used, in which an Immulon-1 plate (Dynatech) was coated first with a conjugate of glutathione and bovine serum albumin (GT-BSA). This conjugate was formed by reacting 2 mg of reduced glutathione (Sigma G-4251) dissolved in 500 μl PBS with 2 mg maleimide activated BSA (Pierce 77115H) dissolved in 200 μl water for 2 hours at room temperature. The mixture containing the modified BSA was diluted 1/1400 in EIA coating buffer (0.1 M sodium carbonate, pH 9.5), and each well of the 96-well plate was coated with 50 μl overnight at room temperature. The plate was blocked as described above, washed, and each well was exposed to 300 ng GST-ICA-12 fusion protein dissolved in 50 μl blott/Tween for 1 hour at room temperature. Incubation with human sera, washing, and development were done as described above.

The present invention has been particularly described and exemplified above. It is contemplated that many other variations and modifications of the invention can be made without departing from the spirit and scope hereof.

What is claimed is:

1. A method of diagnosing insulin dependent diabetes mellitus in a patient, comprising the steps of contacting a blood sample obtained from such patient with a polypeptide reagent comprising the amino acid sequence encoded by the DNA insert of a recombinant cloning vehicle selected from the group consisting of ATCC 40550, 40551, 40552, 40553, 40554, 40703, 40704, 40705, 40706, and 75030, or a fragment of such sequence, said fragment being capable of binding an islet cell autoantibody, and determining binding of antibody from the patient's blood sample to the polypeptide reagent, wherein the presence of said binding indicates a positive result.

2. The method according to claim 1, wherein the polypeptide reagent comprises the amino acid sequence encoded by the DNA insert of recombinant cloning vehicle ATCC 40550, or a fragment of such polypetide, said fragment being capable of binding an islet cell autoantibody.

3. The method according to claim 1, wherein the polypeptide reagent comprises the amino acid sequence encoded by the DNA insert of recombinant cloning vehicle ATCC 40550.

4. The method according to claim 1, wherein the polypeptide reagent comprises the amino acid sequence encoded by the DNA insert of recombinant cloning vehicle ATCC 40551, or a fragment of such polypeptide, said fragment being capable of binding an islet cell autoantibody.

5. The method according to claim 1, wherein the polypeptide reagent comprises the amino acid sequence encoded by the DNA insert of recombinant cloning vehicle ATCC 40551.

6. The method according to claim 1, wherein the polypeptide reagent comprises the amino acid sequence encoded by the DNA insert of recombinant cloning vehicle ATCC 40552, or a fragment of such polypeptide, said fragment being capable of binding an islet cell autoantibody.

7. The method according to claim 1, wherein the polypeptide reagent comprises the amino acid sequence encoded by the DNA insert of recombinant cloning vehicle ATCC 40552.

8. The method according to claim 1, wherein the polypeptide reagent comprises the amino acid sequence encoded by DNA insert of recombinant cloning vehicle ATCC 40553, or a fragment of such polypetide, said fragment being capable of binding an islet cell autoantibody.

9. The method according to claim 1, wherein the polypeptide reagent comprises the amino acid sequence encoded by the DNA insert of recombinant cloning vehicle ATCC 40553.

10. The method according to claim 1, wherein the polypeptide reagent comprises the amino acid sequence encoded by the DNA insert of recombinant cloning vehicle ATCC 40554, or a fragment of such polypeptide, said fragment being capable of binding an islet cell autoantibody.

11. The method according to claim 1, wherein the polypeptide reagent comprises the amino acid sequence encoded by the DNA insert of recombinant cloning vehicle ATCC 40554.

12. The method according to claim 1, wherein the polypeptide reagent comprises the amino acid sequence encoded by the DNA insert of recombinant cloning vehicle ATCC 40703, or a fragment of such polypeptide, said fragment being capable of binding an islet cell autoantibody.

13. The method according to claim 1, wherein the polypeptide reagent comprises the amino acid sequence encoded by the DNA insert of recombinant cloning vehicle ATCC 40703.

14. The method according to claim 1, wherein the polypeptide reagent comprises the amino acid sequence encoded by the DNA insert of recombinant cloning vehicle ATCC 40704, or a fragment of such polypeptide, said fragment being capable of binding an islet cell autoantibody.

15. The method according to claim 1, wherein the polypeptide reagent comprises the amino acid sequence encoded by the DNA insert of recombinant cloning vehicle ATCC 40704.

16. The method according to claim 1, wherein the polypeptide reagent comprises the amino acid sequence encoded by the DNA insert of recombinant cloning vehicle ATCC 40705, or a fragment of such polypeptide, said fragment being capable of binding an islet cell autoantibody.

17. The method according to claim 1, wherein the polypeptide reagent comprises the amino acid sequence encoded by the DNA insert of recombinant cloning vehicle ATCC 40705.

18. The method according to claim 1, wherein the polypeptide reagent comprises the amino acid sequence encoded by the DNA insert of recombinant cloning vehicle ATCC 40706, or a fragment of such polypeptide, said fragment being capable of binding an islet cell autoantibody.

19. The method according to claim 1, wherein the polypeptide reagent comprises the amino acid sequence encoded by the DNA insert of recombinant cloning vehicle ATCC 40706.

20. The method according to claim 1, wherein the polypeptide reagent comprises the amino acid sequence encoded by the DNA insert of recombinant cloning vehicle ATCC 75030, or a fragment of such polypeptide, said fragment being capable of binding an islet cell autoantibody.

21. The method according to claim 1, wherein the polypeptide reagent comprises the amino acid sequence encoded by the DNA insert of recombinant cloning vehicle ATCC 75030.

22. A method for the detecting the presence of T-cells or B-cells that are involved in insulin dependent diabetes mellitus (IDDM) in a human blood sample, comprising the steps of contacting the blood sample with a polypeptide reagent comprising the amino acid sequence encoded by a DNA insert of a recombinant cloning vehicle selected from the group consisting of ATCC 40550, 40551, 40552, 40553, 40554, 40703, 40704, 40705, 40706, and 75030, or a fragment of such sequence, said fragment being capable of binding a T-cell or B-cell involved in IDDM, and determining binding between said polypeptide reagent and T-cells or B-cells from the blood sample, wherein the presence of said binding indicates a positive result.

23. The method according to claim 22, wherein the polypeptide reagent comprises the amino acid sequence encoded by the DNA insert of recombinant cloning vehicle ATCC 40550, or a fragment of such polypeptide, said fragment being capable of binding a T-cell or B-cell involved in IDDM.

24. The method according to claim 22, wherein the polypeptide reagent comprises the amino acid sequence encoded by the DNA insert of recombinant cloning vehicle ATCC 40550.

25. The method according to claim 22, wherein the polypeptide reagent comprises the amino acid sequence encoded by the DNA insert of recombinant cloning vehicle ATCC 40551, or a fragment of such polypeptide, said fragment being capable of binding a T-cell or B-cell involved in IDDM.

26. The method according to claim 22, wherein the polypeptide reagent comprises the amino acid sequence encoded by the DNA insert of recombinant cloning vehicle ATCC 40551.

27. The method according to claim 22, wherein the polypeptide reagent comprises the amino acid sequence encoded by the DNA insert of recombinant cloning vehicle ATCC 40552, or a fragment of such polypeptide, said fragment being capable of binding a T-cell or B-cell involved in IDDM.

28. The method according to claim 22, wherein the polypeptide reagent comprises the amino acid sequence encoded by the DNA insert of recombinant cloning vehicle ATCC 40552.

29. The method according to claim 22, wherein the polypeptide reagent comprises the amino acid sequence encoded by the DNA insert of recombinant cloning vehicle ATCC 40553, or a fragment of such polypeptide, said fragment being capable of binding a T-cell or B-cell involved in IDDM.

30. The method according to claim 22, wherein the polypeptide reagent comprises the amino acid sequence encoded by the DNA insert of recombinant cloning vehicle ATCC 40553.

31. The method according to claim 22, wherein the polypeptide reagent comprises the amino acid sequence encoded by the DNA insert of recombinant cloning vehicle ATCC 40554, or a fragment of such polypeptide, said fragment being capable of binding a T-cell or B-cell involved in IDDM.

32. The method according to claim 22, wherein the polypeptide reagent comprises the amino acid sequence encoded by the DNA insert of recombinant cloning vehicle ATCC 40554.

33. The method according to claim 22, wherein the polypeptide reagent comprises the amino acid sequence encoded by the DNA insert of recombinant cloning vehicle ATCC 40703, or a fragment of such polypeptide, said fragment being capable of binding a T-cell or B-cell involved in IDDM.

34. The method according to claim 22, wherein the polypeptide reagent comprises the amino acid sequence encoded by the DNA insert of recombinant cloning vehicle ATCC 40703.

35. The method according to claim 22, wherein the polypeptide reagent comprises the amino acid sequence encoded by the DNA insert of recombinant cloning vehicle ATCC 40704, or a fragment of such polypeptide, said fragment being capable of binding a T-cell or B-cell involved in IDDM.

36. The method according to claim 22, wherein the polypeptide reagent comprises the amino acid sequence encoded by the DNA insert of recombinant cloning vehicle ATCC 40704.

37. The method according to claim 22, wherein the polypeptide reagent comprises the amino acid sequence encoded by the DNA insert of recombinant cloning vehicle ATCC 40705, or a fragment of such polypeptide, said fragment being capable of binding a T-cell or B-cell involved in IDDM.

38. The method according to claim 22, wherein the polypeptide reagent comprises the amino acid sequence encoded by the DNA insert of recombinant cloning vehicle ATCC 40705.

39. The method according to claim 22, wherein the polypeptide reagent comprises the amino acid sequence encoded by the DNA insert of recombinant cloning vehicle ATCC 40706, or a fragment of such polypeptide, said fragment being capable of binding a T-cell or B-cell involved in IDDM.

40. The method according to claim 22, wherein the polypeptide reagent comprises the amino acid sequence encoded by the DNA insert of recombinant cloning vehicle ATCC 40706.

41. The method according to claim 22, wherein the polypeptide reagent comprises the amino acid sequence encoded by the DNA insert of recombinant cloning vehicle ATCC 75030, or a fragment of such polypeptide, said fragment being capable of binding a T-cell or B-cell involved in IDDM.

42. The method according to claim 22, wherein the polypeptide reagent comprises the amino acid sequence encoded by the DNA insert of recombinant cloning vehicle ATCC 75030.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 1397 nucleotides
        (B) TYPE: nucleic acid
        (C) STRANDEDNESS: single
        (D) TOPOLOGY: linear (xi) SEQUENCE DESCRIPTION: SEQ ID NO: 1:

```
GG CCC ATG AAC GCC TTC ATG GTG TGG GCC AAG                              32
   Pro Met Asn Ala Phe Met Val Trp Ala Lys
                 5                      10

GAT GAG CGG AGG AAG ATC CTG CAA GCC TTC                                 62
Asp Glu Arg Arg Lys Ile Leu Gln Ala Phe
                15                      20

CCA GAC ATG CAC AAC TCC AGC ATC AGC AAG                                 92
Pro Asp Met His Asn Ser Ser Ile Ser Lys
                25                      30

ATC CTT GGA TCT CGC TGG AAG TCC ATG ACC                                122
Ile Leu Gly Ser Arg Trp Lys Ser Met Thr
                35                      40

AAC CAG GAG AAN CAG CCC TAC TAT GAG GAA                                152
Asn Gln Glu Xaa Gln Pro Tyr Tyr Glu Glu
                45                      50

CAG GCT CTG CTG ATC GTC ATC ACC TGG AGA                                182
Gln Ala Leu Leu Ile Val Ile Thr Trp Arg
                55                      60

AGT ATC CTG ACT ACA AGT ACA AGC CGC GGC                                212
Ser Ile Leu Thr Thr Ser Thr Ser Arg Gly
                65                      70

CAA GCG CAC CTG CAT CGT GGA GGG CAA GCG                                242
Gln Ala His Leu His Arg Gly Gly Gln Ala
                75                      80

GCT GCG CGT GGG AGA GTA CAA GGC CCT GAT                                272
Ala Ala Arg Gly Arg Val Gln Gly Pro Asp
                85                      90

GAG GAC CCG GCG TCA GGA TGC CCG CCA GAG                                302
Glu Asp Pro Ala Ser Gly Cys Pro Pro Glu
                95                     100

CTA CGT GAT CCC CCC GCA GGC TGG CCA GGT                                332
Leu Arg Asp Pro Pro Ala Gly Trp Pro Gly
```

|  |  |
|---|---|
| GCA GAT GAG CTC CTC AGA TGT CCT GTA CCC<br>Ala Asp Glu Leu Leu Arg Cys Pro Val Pro<br>                    115                      120 | 362 |
| TCG GGC AGC AGG CAT GCC GCT GCA CAG CCA<br>Ser Gly Ser Arg His Ala Ala Ala Gln Pro<br>                    125                      130 | 392 |
| CTG GTG GAG CAC TAT GTC CCT CGT AGC CTG<br>Leu Val Glu His Tyr Val Pro Arg Ser Leu<br>                    135                      140 | 422 |
| GAC CCC AAC ATG CCT GTG ATC GTC AAC ACC<br>Asp Pro Asn Met Pro Val Ile Val Asn Thr<br>                    145                      150 | 452 |
| TGC AGC CTC AGA GAG GAG GGT GAG GGC ACA<br>Cys Ser Leu Arg Glu Glu Gly Glu Gly Thr<br>                    155                      160 | 482 |
| GAT GAC AGG CAC TCG GTG GCT GAT GGC GAG<br>Asp Asp Arg His Ser Val Ala Asp Gly Glu<br>                    165                      170 | 512 |
| ATG TAC CGG TAC AGC GAG GAC GAG GAC TCG<br>Met Tyr Arg Tyr Ser Glu Asp Glu Asp Ser<br>                    175                      180 | 542 |
| GAG GGT GAA GAG AAG AGC GAT GGG GAG TTG<br>Glu Gly Glu Glu Lys Ser Asp Gly Glu Leu<br>                    185                      190 | 572 |
| GTG GTG CTC ACA GAC TGATCCCGGC TGGGTGGCCT<br>Val Val Leu Thr Asp<br>                    195 | 607 |
| GGCCCCTTCT CCTCTGGGGA AGACCTTGTC CCAACTCGAT | 647 |
| GGGCACAGCC AGCCAACCTA AGACTATGTT GGTACTTGGA | 687 |
| CTTGTTCGTG CCCCAGAGAT GGGCAAAGCT GTGCACTTGC | 727 |
| AGATACATTC ATGAGGGGAG AGGCTCTCTC CCTTCCTGAG | 767 |
| GAGCTGTTGG CCTGGGTGGG CAGGAACTGC AGTATGGCCA | 807 |
| TGGGCTGAGC AGGCTGAGCA CCTCAGCCTT TAGGGCTTAT | 847 |
| GGCCAGGGGA CACTGTATGA CTCTCCTCTC CTGCAGGTGT | 887 |
| CTATCCACCT GGGGTATGGC ATCTACCGAC CTGTCTCCCT | 927 |
| GGGGTCACAT GCTTTGTTTC AGGCTTGTC CTGGCTGGAC | 967 |
| CAGCCACTGT GGGACCAACA CCCCTCCCAC ACTCCCCCAG | 1007 |
| ACTGCTCGTC TATCACCAGG ATCGCTTTGT ACTTTGTGCA | 1047 |
| AAAGGGTCTG GCTGTCCCTT GCTGTTTTCA TCTCTGCCAA | 1087 |
| GCCTATTGTG CCTCTGGCTG CTGTATGTGT GCGCGTGCAC | 1127 |
| GTGTGTGTGT TTCATCTGTT CATTCACTGC ACAGAGTATT | 1167 |
| TATTGTGTGC CCACTACGTG CCAGGCACTG TTGCTGAGTT | 1207 |
| CCTGTGGGTG TGTCTCTCGA TGCCACTCCT GCTTCTCTGG | 1247 |
| GGGCCTCTTT CTGTGCTTCT CTTTGTCCCC AAATTGCTAC | 1287 |
| CTCTTTGTCA GTCTGGGTGT CTCAGGTTCT GTGTGTCCTT | 1327 |
| GTGTGCATTT CTGTCTCTCT CTGTCCTCGT CTCTCTGCAA | 1367 |
| GGCCCTCTAT TTCTCTCTTT CTTGGTGTCT | 1397 |

(2) INFORMATION FOR SEQ ID NO: 2:

(i) SEQUENCE CHARACTERISTICS:
        (A) LENGTH: 5051 nucleotides
        (B) TYPE: nucleic acid
        (C) STRANDEDNESS: single
        (D) TOPOLOGY: linear (xi) SEQUENCE DESCRIPTION: SEQ ID NO: 2:

```
GGCAGAGCTT GAAGA ATG TCT TCC AAG CAA                                    30
              Met Ser Ser Lys Gln
                              5

GCC ACC TCT CCA TTT GCC TGT GCA GCT GAT                                 60
Ala Thr Ser Pro Phe Ala Cys Ala Ala Asp
             10                      15

GGA GAG GAT GCA ATG ACC CAG GAT TTA ACC                                 90
Gly gln Asp Ala Met Thr Gln Asp Leu Thr
             20                      25

TCA AGG GAA AAG GAA GAG GGC AGT GAT CAA                                120
Ser Arg Glu Lys Glu Glu Gly Ser Asp Gln
             30                      35

CAT GTG GCC TCC CAT CTG CCT CTG CAC CCC                                150
His Val Ala Ser His Leu Pro Leu His Pro
             40                      45

ATA ATG CAC AAC AAA CCT CAC TCT GAG GAG                                180
Ile Met His Asn Lys Pro His Ser Glu Glu
             50                      55

CTA CCA ACA CTT GTC AGT ACC ATT CAA CAA                                210
Leu Pro Thr Leu Val Ser Thr Ile Gln Gln
             60                      65

GAT GCT GAC TGG GAC AGC GTT CTG TCA TCT                                240
Asp Ala Asp Trp Asp Ser Val Leu Ser Ser
             70                      75

CAG CAA AGA ATG GAA TCA GAG AAT AAT AAG                                270
Gln Gln Arg Met Glu Ser Gln Asn Asn Lys
             80                      85

TTA TGT TCC CTA TAT TCC TTC CGA AAT ACC                                300
Leu Cys Ser Leu Tyr Ser Phe Arg Asn Thr
             90                      95

TCT ACC TCA CCA CAT AAG CCT GAC GAA GGG                                330
Ser Thr Ser Pro His Lys Pro Asp Glu Gly
            100                     105

AGT CGG GAC CGT GAG ATA ATG ACC AGT GTT                                360
Ser Arg Asp Arg Glu Ile Met Thr Ser Val
            110                     115

ACT TTT GGA ACC CCA GAG CGC CGC AAA GGG                                390
Thr Phe Gly Thr Pro Glu Arg Arg Lys Gly
            120                     125

AGT CTT GCC GAT GTG GTG GAC ACA CTG AAA                                420
Ser Leu Ala Asp Val Val Asp Thr Leu Lys
            130                     135

CAG AAG AAG CTT GAG GAA ATG ACT CGG ACT                                450
Gln Lys Lys Leu Glu Glu Met Thr Arg Thr
            140                     145

GAA CAA GAG GAT TCC TCC TGC AGT GAA AAA                                480
Glu Gln Glu Asp Ser Ser Cys Met Glu Lys
            150                     155

CTA CTT TCA AAA GAT TGG AAG GAA AAA ATG                                510
Leu Leu Ser Lys Asp Trp Lys Glu Lys Met
            160                     165

GAA AGA CTA AAT ACC AGT GAA CTT CTT GGA                                540
```

```
                                                            -continued

Glu Arg Leu Asn Thr Ser Glu Leu Leu Gly
            170                 175

GAA ATT AAA GGT ACA CCT GAG AGC CTG GCA                              570
Glu Ile Lys Gly Thr Pro Glu Ser Leu Ala
            180                 185

GAA AAA GAA CGG CAG CTC TCC ACC ATG ATT                              600
Glu Lys Glu Arg Gln Leu Ser Thr Met Ile
            190                 195

ACC CAG CTG ATC AGT TTA CGG GAG CAG CTA                              630
Thr Gln Leu Ile Ser Leu Arg Glu Gln Leu
            200                 205

CTG GCA GCG CAT GAT GAA AGA AAA AAA CTG                              660
Leu Ala Ala His Asp Glu Gln Lys Lys Leu
            210                 215

GCA GCG TCA CAA ATT GAG AAA CAA CGG CAG                              690
Ala Ala Ser Gln Ile Glu Lys Gln Arg Gln
            220                 225

CAA ATG GAC CTT GCT CGC CAA CAG CAA GAA                              720
Gln Met Asp Leu Ala Arg Gln Gln Gln Glu
            230                 235

CAG ATT GCG AGA CAA CAG CAG CAA CTT CTG                              750
Gln Ile Ala Arg Gln Gln Gln Gln Leu Leu
            240                 245

CAA CAG CAG CAC AAA ATT AAT CTC CTG CAG                              780
Gln Gln Gln His Lys Ile Asn Leu Leu Gln
            250                 255

CAA CAG ATC CAG GTT CAG GGT CAC ATG CCT                              810
Gln Gln Ile Gln Val Gln Gly His Met Pro
            260                 265

CCG CTC ATG ATC CCA ATT TTT CCA CAT GAC                              840
Pro Leu Met Ile Pro Ile Phe Pro His Asp
            270                 275

CAG CGG ACT CTG GCA GCA GCT GCT GCT GCC                              870
Gln Arg Thr Leu Ala Ala Ala Ala Ala Ala
            280                 285

CAA CAG GGA TTC CTC TTC CCC CCT GGA ATA                              900
Gln Gln Gly Phe Leu Phe Pro Pro Gly Ile
            290                 295

ACA TAC AAA CCA GGT GAT AAC TAC CCC GTA                              930
Thr Tyr Lys Pro Gly Asp Asn Tyr Pro Val
            300                 305

CAG TTC ATT CCA TCA ACA ATG GCA GCT GCT                              960
Gln Phe Ile Pro Ser Thr Met Ala Ala Ala
            310                 315

GCT GCT TCT GGA CTC AGC CCT TTA CAG CTC                              990
Ala Ala Ser Gly Leu Ser Pro Leu Gln Leu
            320                 325

CAG AAG GGT CAT GTC TCC CAC CCA CAA ATT                             1020
Gln Lys Gly His Val Ser His Pro Gln Ile
            330                 335

AAC CAA AGG CTA AAG GGC CTA AGT GAC CGT                             1050
Asn Gln Arg Leu Lys Gly Leu Ser Asp Arg
            340                 345

TTT GGC AGG AAT TTG GAC ACC TTT GAA CAT                             1080
Phe Gly Arg Asn Leu Asp Thr Phe Glu His
            350                 355

GGT GGT GGC CAC TCT TAC AAC CAC AAA CAG                             1110
Gly Gly Gly His Ser Tyr Asn His Lys Gln
            360                 365
```

|  |  |
|---|---|
| ATT GAG CAG CTC TAT GCC GCT CAG CTG GCC<br>Ile Glu Gln Leu Tyr Ala Ala Gln Leu Ala<br>370                     375 | 1140 |
| AGC ATG CAG GTG TCA CCT GGA GCA AAG ATG<br>Ser Met Gln Val Ser Pro Gly Ala Lys Met<br>380                     385 | 1170 |
| CCA TCA ACT CCA CAG CCA CCA AAC ACA GCA<br>Pro Ser Thr Pro Gln Pro Pro Asn Thr Ala<br>390                     395 | 1200 |
| GGG ACG GTC TCA CCT ACT GGG ATA AAA AAT<br>Gly Thr Val Ser Pro Thr Gly Ile Lys Asn<br>400                     405 | 1230 |
| GAA AAG AGA GGG ACC AGC CCT GTA ACT CAA<br>Glu Lys Arg Gly Thr Ser Pro Val Thr Gln<br>410                     415 | 1260 |
| GTT AAG GAT GAA GCA GCA GCA CAG CCT CTG<br>Val Lys Asp Glu Ala Ala Ala Gln Pro Leu<br>420                     425 | 1290 |
| AAT CTC TCA TCC CGA CCC AAG ACA GCA GAG<br>Asn Leu Ser Ser Arg Pro Lys Thr Ala Glu<br>430                     435 | 1320 |
| CCT GTA AAG TCC CCA ACG TCT CCC ACC CAG<br>Pro Val Lys Ser Pro Thr Ser Pro Thr Gln<br>440                     445 | 1350 |
| AAC CTC TTC CCA GCC AGC AAA ACC AGC CCT<br>Asn Leu Phe Pro Ala Ser Lys Thr Ser Pro<br>450                     455 | 1380 |
| GTC AAT CTG CCA AAC AAA AGC AGC ATC CCT<br>Val Asn Leu Pro Asn Lys Ser Ser Ile Pro<br>460                     465 | 1410 |
| AGC CCC ATT GGA GGA AGC CTG GGA AGA GGA<br>Ser Pro Ile Gly Gly Ser Leu Gly Arg Gly<br>470                     475 | 1440 |
| TCC TCT TTA GAT ATC CTA TCT AGT CTC AAC<br>Ser Ser Leu Asp Ile Leu Ser Ser Leu Asn<br>480                     485 | 1470 |
| TCC CCT GCC CTT TTT GGG GAT CAG GAT ACA<br>Ser Pro Ala Leu Phe Gly Asp Gln Asp Thr<br>490                     495 | 1500 |
| GTG ATG AAA GCC ATT CAG GAG GCG CGG AAG<br>Val Met Lys Ala Ile Gln Glu Ala Arg Lys<br>500                     505 | 1530 |
| ATG CGA GAG CAG ATC CAG CGG GAG CAA CAG<br>Met Arg Glu Gln Ile Gln Arg Glu Gln Gln<br>510                     515 | 1560 |
| CAG CAA CAG CCA CAT GGT GTT GAC GGG AAA<br>Gln Gln Gln Pro His Gly Val Asp Gly Lys<br>520                     525 | 1590 |
| CTG TCC TCC ATA AAT AAT ATG GGG CTG AAT<br>Lys Ser Ser Ile Asn Asn Met Gly Leu Asn<br>530                     535 | 1620 |
| AGC TGC AGG AAT GAA AAG GAA AGA ACG CGC<br>Ser Cys Arg Asn Glu Lys Glu Arg Thr Arg<br>540                     545 | 1650 |
| TTT GAG AAT TTG GNN CCC CAG TTA ACG GGA<br>Phe Glu Asn Leu Xaa Pro Gln Leu Thr Gly<br>550                     555 | 1680 |
| AAG TCA AAT GAA GAT GGA AAA CTG GGC CCA<br>Lys Ser Asn Glu Asp Gly Lys Leu Gly Pro<br>560                     565 | 1710 |

| | |
|---|---|
| GGT GTC ATC GAC CTT ACT CGG CCA GAA GAT<br>Gly Val Ile Asp Leu Thr Arg Pro Glu Asp<br>570 575 | 1740 |
| GCA GAG GGA GGT GCC ACT GTG GCT GAA GCA<br>Ala Glu Gly Gly Ala Thr Val Ala Glu Ala<br>580 585 | 1770 |
| CGA GTC TAC AGG GAC GCC CGC GGC CTG CCA<br>Arg Val Tyr Arg Asp Ala Arg Gly Leu Pro<br>590 595 | 1800 |
| GCA GCG AGC CAC ACA TTA AGC GAC CAA<br>Ala Ala Ser His Thr Leu Ser Asp Gln<br>600 | 1827 |
| TGAATGCATT CATGGTTTGG GCAAAGGATG AGAGGAGAAA | 1867 |
| AATCCTTCAG GCCTTCCCCG ACATGCATAA CTCCAACATT | 1907 |
| AGCAAAATCT TAGGATCTCG CTGGAAATCA ATGTCCAACC | 1947 |
| AGGAGAAGCA ACCTTATTAT GAAGAGCAGG CCCGGCTAAG | 1987 |
| CAAGATCCAC TTAGAGAAGT ACCCAAACTA TAAATACAAA | 2027 |
| CCCCGACCGA AACNCACCTG CATTGTTGAT GGCAAAAAGC | 2067 |
| TTCGGATTGG GGAGTATAAG CAACTGATGA GGTCTCGGAG | 2107 |
| ACAGGAGATG AGGCAGTTCT TTACTGTGGG GCAACAGCCT | 2147 |
| CAGATTCCAA TCACCACAGG AACAGGTGTT GTGTATCCTG | 2187 |
| GTGCTATCAC TATGGCAACT ACCACACCAT CGCCTCAGAT | 2227 |
| GACATCTGAC TGCTCTAGCA CCTCGGCCAG CGCGGAGCCC | 2267 |
| AGCCTCCCGG TCATCCAGAG CACTTATGGT ATGAAGACAG | 2307 |
| ATGGCGGAAG CTAGCTGGAA ATGAAATGAT CAATGGAGAG | 2347 |
| GATGAAATGG AAATGTATGA TGACTATGAA GATGACCCCA | 2387 |
| AATCAGACTA TAGCAGTGAA ATGAAGCCC CGGAGGCTGT | 2427 |
| CAGAGCCAAC TGAGGAGTTT TTGTTTGCTG AATTAAAGTA | 2467 |
| CTCTGACATT TCACCCCCCT CCCCAACAAA GAGTTATCCA | 2507 |
| AGAGCCCGCA TGCATTTGTG GCTCCACAAT TACATCAGCA | 2547 |
| GAATGGTCTT AATTGTTTCG TAAAGTGTGA GACAGATTAA | 2587 |
| GTTTTCCCTG ATTTTTCATG AACTTGAGTT TTTTGTTGTT | 2627 |
| ATTGTTATTG TTGTTGTTGT TGTTTTTTTT TTTTGTTGTT | 2667 |
| ATTGTTATTG TTGTTGTTGT TGTTTTTTTA ATTTAGGTGA | 2707 |
| AGACATATTA AATATGAGAC ACCAGGACTT GAAACTTATC | 2747 |
| TCAACCCGTA GATGTCTTAC AAGTCTTATA TTTTTGTCTT | 2787 |
| ACTTTTTTTT TCTTTTGGAT GTTGATAAAG GTTTAAGTTA | 2827 |
| CTGTTTTAGA TGGGGTTAAA CATTCTCACT CAGGTATGCT | 2867 |
| GTGCCGGCCT ACAGGTTGTG AATGTGTTTT TTATTCTGAA | 2907 |
| TTATTTTAGA AAACAACTGA GGATTTCATA TTGTGAAACA | 2947 |
| GGACAAGTCC ACGGCGTGTG CAGCTGCATG TAGAGCATAT | 2987 |
| TCAAAAGGCC TCGGAATTCC AATTTTCCAT TTGTAGAGTT | 3027 |
| AAACTTTGAA TGTGCCAAAC TTTTTCGTAA CTTTTGAATC | 3067 |

| | |
|---|---|
| TTAATATTTT GAAAGTCTTA AAGGAGACAC TGCAAAGTCT | 3107 |
| TAGACAATCT TTGGCATCTT AAAATAAAAT AGCAAACCAA | 3147 |
| CATTTTTTTT TCCAGAAAAT GGTAAGGTAC TCAGGAATCT | 3187 |
| GGAGACAAGA TATTGTAAGG AATGAACAAG GTTGCCACAG | 3227 |
| TGCATGGACC CAATTGTGTT TGCCTGTTGA CGTGCCATCA | 3267 |
| GTGCGTGATG TGGTATGACA TACACACACC AGAGCAACCG | 3307 |
| CCACACCAGA TATCGACAGA GTGGTCTTCT CTGCCTGAGA | 3347 |
| CCACCTCTCA CTACATCCAT TATCCCTTTG CCTTTAACCC | 3387 |
| TGACATTCAG TCTTAACACA TTTTATCTTA AATAATTTAT | 3427 |
| TCATTCCAGA ATGTCAAGGG TCCACTTGCT ATTTATTTTT | 3467 |
| TTTCAATTGT TGGTGCATTA ATTTAATAAT TCTTGTTTTT | 3507 |
| CACCTTCCTT CCCCGAAGAA CTTTTCCGTC CTTTTCACCT | 3547 |
| CCTTCTCCTG TGTACATAGT GATTTTATGT CCCCAGAACG | 3587 |
| CCTGGAAGCA TTTCTGAAAC CAAGATATTA TTAAAAACCT | 3627 |
| ATTATTGTTT TTAATCATGA GTATGTATCT GGCTGCAGGG | 3667 |
| CTGTGTATTG GGATATAGGT ATATAGTCTT ACACTTAAAC | 3707 |
| AGGTATGCCC CTGAGGTTCA CTGTGACCTC AAGTCTTTTG | 3747 |
| CCAGAATTTT CCCCTAATTC AGTTCACAAG TGGTAGGGTC | 3787 |
| TGCATCAGTG GCATTTCCCC CTGAATTCCA TTCAGCAGCA | 3827 |
| AGGTTCAACA GTGGTGACTG CCAGGCAGGA GAGTCCTGCG | 3867 |
| GCCAAACCTG AAGCCCAAGG CTCGTGGGCC ATGCAGGAAT | 3907 |
| CTCAGTGAAG CTGTCATGGG CTGGCACCTT TACACTGAGT | 3947 |
| TGCCTTGTCC CAGCTGGCAC ATCTAGGGAG TTCATTGCAA | 3987 |
| AATCCCCAGG ATGCAAAAAG CCACATGACA GCCTCAGAGC | 4027 |
| AAAGATGGTG GCAAATAGTC ATGATACATC TAGAGAATGA | 4067 |
| AAGAAAACTG TAAGGGAGGA GAAGGAGGGG AATACATTCC | 4107 |
| CTATATGGGA TGTTCCTACT GTTAACCTGT GGGAACAGAT | 4147 |
| AGCTCCGGGG GCAGCAGATG AGTTCCTCTG GCTGACTCTA | 4187 |
| TCTGTAGCCA CATGGGACC TGCCTACGTG TGAACAAAAT | 4227 |
| GAACTGCACT TATCACACAA GGATTTCTTT GAAGACATGC | 4267 |
| TACTGGGGTG GGAAGCAGTG AGGTTTTATT CCCCATCTCC | 4307 |
| TAACTACAGG GAGCTCTGCC ATGTCATTTT GGCCTTCCTG | 4347 |
| AAACTAGGAC AGGTTGTCTA TCGGGGGGCT TCCCCCAGAG | 4387 |
| AGGTTTAGTG GGAGAATGTC AGTGAATGGG ATAGTTCACC | 4427 |
| TCATGGACA ACCCAGAATC TGATCACCAG GACATAGGAA | 4467 |
| TGGCCCCATC AGATTCCTG AGCCATTTTG TCACTTGGAA | 4507 |
| GAAAATAGTG TACCTTTGTA TTTATTTAAG AGTGCTCAAG | 4547 |
| GCCTAATAGC AATAAACAGG TCTAGCCAAG AAATTACAAG | 4587 |
| CTATTCTGTT AGCTGGGAGT GCTCTCTATA AGCTGATTAA | 4627 |
| GGTACTGATA GGAACTCTTT GTTATTCATG TTGGTTGGGG | 4667 |

```
ATTAGAAATT TGTTTTTGTA CATTTATTTC AAATGAGGAG                4707

GAGGTCATTT TTTCTCTCAA AAAATGAGTA TTTATTATTG                4747

TCTTACTGAT TTCTTTGATT ATATACCTCT CCTCCTCAGT                4787

TCACTCTTGT TTTTTTTCTT TCTCTTTGGC TTTTGCTTTT                4827

GCTCTCTCTC ACTTCTTTCT TATTTTGTTG CATTGGTAGA                4867

GTGTTGTATG GCTAGCATTG TATTGTATGT AATTAATTTT                4907

GCACAAAAGC AAACATTTAG CATAGTAGGT TAATTTTGTT                4947

TGTTTTTATG ACCATGCCAA AATAATATTC TGGGCTGGTG                4987

GAGAACAAAG GACTATTCTT TAGGACTGAA ACTTGATTTT                5027

GCTCATAGTA AGTAAAAAAA AAAA                                 5051

(2) INFORMATION FOR SEQ ID NO: 3:

(i) SEQUENCE CHARACTERISTICS:
        (A) LENGTH: 575 nucleotides
        (B) TYPE:   nucleic acid
        (C) STRANDEDNESS: single
        (D) TOPOLOGY:  linear (xi) SEQUENCE DESCRIPTION: SEQ ID NO: 3:

AA ATT GAG AAG CTC AAA CTT GAG ATT GAG AAA                  32
   Ile Glu Lys Leu Lys Leu Glu Ile Glu Lys
                 5                  10

CTG AAA GCT GAA TCT GGG AAT CCA TCT ATT                     62
Leu Lys Ala Glu Ser Gly Asn Pro Ser Ile
             15                  20

CGG CAG AAG ATA CGC TTA AAA GAT AAA GCA                     92
Arg Gln Lys Ile Arg Leu Lys Asp Lys Ala
             25                  30

GCA GAT GCC AAA AAA ATT CAG GAT CTG GAG                    122
Ala Asp Ala Lys Lys Ile Gln Asp Leu Glu
             35                  40

CGA CAA GTT AAG GAA ATG GAA GGG ATT CTG                    152
Arg Gln Val Lys Glu Met Glu Gly Ile Leu
             45                  50

AAG AGA AGA TAT CCC AAT TCT TTA CCT GCT                    182
Lys Arg Arg Tyr Pro Asn Ser Leu Pro Ala
             55                  60

TTA ATA TTG GCT GCA TCA GCA GCT GGT GAT                    212
Leu Ile Leu Ala Ala Ser Ala Ala Gly Asp
             65                  70

ACA GTG GAT AAA AAT ACA GTG GAA TTT ATG                    242
Thr Val Asp Lys Asn Thr Val Glu Phe Met
             75                  80

GAG AAA AGG ATA AAA AAG CTA GAA GCT GAT                    272
Glu Lys Arg Ile Lys Lys Leu Glu Ala Asp
             85                  90

CTG GAG GGC AAA GAT GAA GAT GCA AAG AAA                    302
Leu Glu Gly Lys Asp Glu Asp Ala Lys Lys
             95                 100

AGC CTT CGT ACC ATG GAA CAA CAG TTT CAG                    332
Ser Leu Arg Thr Met Glu Gln Gln Phe Gln
            105                 110

AAA ATG AAG ATT CAG TAT GAA CAA AGA CTA                    362
Lys Met Lys Ile Gln Tyr Glu Gln Arg Leu
            115                 120
```

```
GAG CAG CAG GAG CAG CTA CTT GCC TGC AAA                                392
Glu Gln Gln Glu Gln Leu Leu Ala Cys Lys
                125                 130

TTG AAT CAA CAT GAC TCT CCC AGA ATT AAA                                422
Leu Asn Gln His Asp Ser Pro Arg Ile Lys
                135                 140

GCC CTA GAG AAG GAA CTT GAT GAC ATC AAG                                452
Ala Leu Glu Lys Glu Leu Asp Asp Ile Lys
                145                 150

GAA GCC CAT CAG ATC ACT GTA AGA AAC CTT                                482
Glu Ala His Gln Ile Thr Val Arg Asn Leu
                155                 160

GAA GCC GAA ATA GAC GTT CTT AAA CAT CAG                                512
Glu Ala Glu Ile Asp Val Leu Lys His Gln
                165                 170

AAT GCT GAA TTA GAC GTC AAG AAA AAT GAT                                542
Asn Ala Glu Leu Asp Val Lys Lys Asn Asp
                175                 180

AAA GAT GAT GAA GAT TTT CAG TCT ATA GAA                                572
Lys Asp Asp Glu Asp Phe Gln Ser Ile Glu
                185                 190

TTC                                                                    575
Phe (2) INFORMATION FOR SEQ ID NO: 4:

(i) SEQUENCE CHARACTERISTICS:
        (A) LENGTH: 794 nucleotides
        (B) TYPE: nucleic acid
        (C) STRANDEDNESS: single
        (D) TOPOLOGY: linear (xi) SEQUENCE DESCRIPTION: SEQ ID NO: 4:

GC GAT ACA CCG GGC GTT AAA GTG GGT GAT GAA                              32
   Asp Thr Pro Cys Val Lys Val Gly Asp Glu
               5                   10

GTG GAG GTA ATG GTT GTT GAA AAA GAA GAC                                 62
Val Glu Val Met Val Val Glu Lys Glu Asp
                15                  20

CGT AAC GGC AAT TTA AAC CTA AGC CGT AAA                                 92
Arg Asn Gly Asn Leu Asn Leu Ser Arg Lys
                25                  30

AGT GCC CGC ATT TTC CGT GCT TGG GAA AGA                                122
Ser Ala Arg Ile Phe Arg Ala Trp Glu Arg
                35                  40

ATT ATG GAA GTG CAT AAA ACA GGT GAA GTG                                152
Ile Met Glu Val His Lys Thr Gly Glu Val
                45                  50

GTT ACA GGT TTG GTT ACC AGC AAA ACA AAA                                182
Val Thr Gly Leu Val Thr Ser Lys Thr Lys
                55                  60

GGT GGC TTG ATT GTA GAT GTT TTC GGT ATG                                212
Gly Gly Leu Ile Val Asp Val Phe Gly Met
                65                  70

GAA ACT TTC TTA CCG GGT TCT CAA ATT GAT                                242
Glu Thr Phe Leu Pro Gly Ser Gln Ile Asp
                75                  80

GTT AAA CCC GTT ACA GAT TAC GAC CAG TTT                                272
Val Lys Pro Val Thr Asp Tyr Asp Gln Phe
                85                  90
```

```
                                                    -continued

GTT GGT AAA ACA ATG GAG TTT AAA GTT GTT              302
Val Gly Lys Thr Met Glu Phe Lys Val Val
             95                  100

AAG ATT AAC GAA ACA ATT AAG AAT GCT GTT              332
Lys Ile Asn Glu Thr Ile Lys Asn Ala Val
            105                  110

GTA TCT CAC AAA GCA TTA ATT GAA AGC GAT              362
Val Ser His Lys Ala Leu Ile Glu Ser Asp
            115                  120

ATT GAA GCA CAA CGT GCT GAA ATA ATG AGC              392
Ile Glu Ala Gln Arg Ala Glu Ile Met Ser
            125                  130

AAA TTA GAA AAA GGT CAG GTG TTA GAA GGT              422
Lys Leu Glu Lys Gly Gln Val Leu Glu Gly
            135                  140

ACT GTT AAG AAC ATT ACA GAC TTC GGT GCA              452
Thr Val Lys Asn Ile Thr Asp Phe Gly Ala
            145                  150

TTT ATG GAC CTT GGT GGC TTA GAC GGC TTA              482
Phe Met Asp Leu Gly Gly Leu Asp Gly Leu
            155                  160

TTA TAC ATT ACA GAT ATT TCA TGG GGC AGA              512
Leu Tyr Ile Thr Asp Ile Ser Trp Gly Arg
            165                  170

ATT TCT CAC CCA AGC GAA GTA TTG AAA ATG              542
Ile Ser His Pro Ser Glu Val Leu Lys Met
            175                  180

GAT CAG AAA TTA AAT GTG GTT GTA TTA GAC              572
Asp Gln Lys Leu Asn Val Val Val Leu Asp
            185                  190

TTT GAT GAT GAT AAA AAA CGT ATC AGC CTT              602
Phe Asp Asp Asp Lys Lys Arg Ile Ser Leu
            195                  200

GGT TTA AAA CAA TTA ACA CCG CAT CCT TGG              632
Gly Leu Lys Gln Leu Thr Pro His Pro Trp
            205                  210

GAA GTA TTA CCT GAA GGT TTG GCT GAA GGT              662
Glu Val Leu Pro Glu Gly Leu Ala Glu Gly
            215                  220

GCT ATT GTA AAA GGT AAA GTG GTA AAT ATT              692
Ala Ile Val Lys Gly Lys Val Val Asn Ile
            225                  230

GAA GAT TAC GGT GCA TTC TTA GAA ATT CAA              722
Glu Asp Tyr Gly Ala Phe Leu Glu Ile Gln
            235                  240

CCG GGG GTT GAA GGT TTG GTT CAC GTA AGT              752
Pro Gly Val Glu Gly Leu Val His Val Ser
            245                  250

GAA ATT ACC TGG GAA AAT ACA CCA ATC AAC              782
Glu Ile Thr Trp Glu Asn Thr Pro Ile Asn
            255                  260

GCT AAA GAA TTC                                      794
Ala Lys Glu Phe
```

(2) INFORMATION FOR SEQ ID NO: 5:

(i) SEQUENCE CHARACTERISTICS:
        (A) LENGTH: 1570 nucleotides
        (B) TYPE: nucleic acid
        (C) STRANDEDNESS: single
        (D) TOPOLOGY: linear (xi) SEQUENCE DESCRIPTION: SEQ ID NO: 5:

```
  G GAT GGC TCC CCC AAC ACC CCC TTC CGT AAG                              31
    Asp Gly Ser Pro Asn Thr Pro Phe Arg Lys
                  5                      10

GAC CTC ATC AGC CTG GAC TCA TCC CCA GCC                                  61
Asp Leu Ile Ser Leu Asp Ser Ser Pro Ala
                15                      20

AAG GAG CGG CTG GAG GAC GGC TGT GTG CAC                                  91
Lys Glu Arg Leu Glu Asp Gly Cys Val His
                25                      30

CCA CTG GAG GAA GCC ATG CTG AGC TGC GAC                                 121
Pro Leu Glu Glu Ala Met Leu Ser Cys Asp
                35                      40

ATG GAT GGC TCC CGC CAC TTC CCC GAG TCC                                 151
Met Asp Gly Ser Arg His Phe Pro Glu Ser
                45                      50

CGA AAC AGC AGC CAC ATC AAG AGG CCC ATG                                 181
Arg Asn Ser Ser His Ile Lys Arg Pro Met
                55                      60

AAC GCC TTC ATG GTG TGG GCC AAG GAT GAG                                 211
Asn Ala Phe Met Val Trp Ala Lys Asp Glu
                65                      70

CGG AGG AAG ATC CTG CAA GCC TTC CCA GAC                                 241
Arg Arg Lys Ile Leu Gln Ala Phe Pro Asp
                75                      80

ATG CAC AAC TCC AGC ATC AGC AAG ATC CTT                                 271
Met His Asn Ser Ser Ile Ser Lys Ile Leu
                85                      90

GGA TCT CGC TGG AAG TCC ATG ACC AAC CAG                                 301
Gly Ser Arg Trp Lys Ser Met Thr Asn Gln
                95                     100

GAG AAG CAG CCC TAC TAT GAG GAA CAG GCT                                 331
Glu Lys Gln Pro Tyr Tyr Glu Glu Gln Ala
               105                     110

CTG CTG ATC GTC ATC ACC TGG AGA AGT ATC                                 361
Leu Leu Ile Val Ile Thr Trp Arg Ser Ile
               115                     120

CTG ACT ACA AGT ACA AGC CGC GGC CAA GCG                                 391
Leu Thr Thr Ser Thr Ser Arg Gly Gln Ala
               125                     130

CAC CTG CAT CGT GGA GGG CAA GCG GCT GCG                                 421
His Leu His Arg Gly Gly Gln Ala Ala Ala
               135                     140

CGT GGG AGA GTA CAA GGC CCT GAT GAG GAC                                 451
Arg Gly Arg Val Gln Gly Pro Asp Glu Asp
               145                     150

CCG GCG TCA GGA TGC CCG CCA GAG CTA CGT                                 481
Pro Ala Ser Gly Cys Pro Pro Glu Leu Arg
               155                     160

GAT CCC CCC GCA GGC TGG CCA GGT GCA GAT                                 511
Asp Pro Pro Ala Gly Trp Pro Gly Ala Asp
               165                     170

GAG CTC CTC AGA TGT CCT GTA CCC TCG GGC                                 541
Glu Leu Leu Arg Cys Pro Val Pro Ser Gly
               175                     180

AGC AGG CAT GCC GCT GCA CAG CCA CTG GTG                                 571
Ser Arg His Ala Ala Ala Gln Pro Leu Val
               185                     190
```

```
GAG CAC TAT GTC CCT CGT AGC CTG GAC CCC                              601
Glu His Tyr Val Pro Arg Ser Leu Asp Pro
                195                 200

AAC ATG CCT GTG ATC GTC AAC ACC TGC AGC                              631
Asn Met Pro Val Ile Val Asn Thr Cys Ser
                205                 210

CTC AGA GAG GAG GGT GAG GGC ACA GAT GAC                              661
Leu Arg Glu Glu Gly Glu Gly Thr Asp Asp
                215                 220

AGG CAC TCG GTG GCT GAT GGC GAG ATG TAC                              691
Arg His Ser Val Ala Asp Gly Glu Met Tyr
                225                 230

CGG TAC AGC GAG GAC GAG GAC TCG GAG GGT                              721
Arg Tyr Ser Glu Asp Glu Asp Ser Glu Gly
                235                 240

GAA GAG AAG AGC GAT GGG GAG TTG GTG GTG                              751
Glu Glu Lys Ser Asp Gly Glu Leu Val Val
                245                 250

CTC ACA GAC TGATCCCGGC TGGGTGGCCT                                    780
Leu Thr Asp

GGCCCCTTCT CCTCTGGGGA AGACCTTGTC CCAACTCGAT                          820

GGGCAAAGCT AGCCAACCTA AGACTATGTT GGTACTTGGA                          860

CTTGTTCGTG CCCCAGAGAT GGGCAAAGCT GTGCACTTGC                          900

AGATACATTC ATGAGGGGAG AGGCTCTCTC CCTTCCTGAG                          940

GAGCTGTTGG CCTGGGTGGG CAGGAACTGC AGTATGGCCA                          980

TGGGCTGAGC AGGCTGAGCA CCTCAGCCTT TAGGGCTTAT                         1020

GGCCAGGGGA CACTGTATGA CTCTCCTCTC CTGCAGGTGT                         1060

CTATCCACCT GGGGTATGGC ATCTACCGAC CTGTCTCCCT                         1100

GGGGTCACAT GCTTTGTTTC CATTCTTGTC CTGGCTGGAC                         1140

CAGCCACTGT GGGACCAACA CCCCTCCCAC ACTCCCCCAG                         1180

ACTGCTCGTC TATCACCAGG ATCGCTTTGT ACTTTGTGCA                         1220

AAAGGGTCTG GCTGTCCCTT GCTGTTTTCA TCTCTGCCAA                         1260

GCCTATTGTG CCTCTGGCTG CTGTATGTGT GCGCGTGCAC                         1300

GTGTGTGTGT TTCATCTGTT CATTCACTGC ACAAGATATT                         1340

TATTGAGTGC CCACTACGTG CCAGGCACTG TTGCTGAGTT                         1380

CCTGTGGGTG TGTCTCTCGA TGCCACTCCT GCTTCTCTGG                         1420

GGGCCTCTTT CTGTGCTTCT CTTTGTCCCC AAATTGCTAC                         1460

CTCTTTGTCA GTCTGGGTGT CTCAGGTTCT GTGTGTCCTT                         1500

GTGTGCATTT CTGTCTCTCT CTGTCCTCGT CTCTCTGCAA                         1540

GGCCCTCTAT TTCTCTCTTT CTTGGTGTCT                                    1570

(2) INFORMATION FOR SEQ ID NO: 6:

(i) SEQUENCE CHARACTERISTICS:
        (A) LENGTH: 3243 nucleotides
        (B) TYPE: nucleic acid
        (C) STRANDEDNESS: single
        (D) TOPOLOGY: linear (xi) SEQUENCE DESCRIPTION: SEQ ID NO: 6:

CCAGAACCCA AGAGACCAGG AGTGTCGGAG GCTGCCTCTG                            40
```

```
GAAGCCAGGA GAAGCTGGAC TTCAACCGAA ATTTGAAAGA              80

AGTGGTGCCA GCCATAGAGA AGCTGTTGTC CAGTGACTGG             120

AAGGAGAGGT TTCTAGGAAG GAACTCTATG GAAGCCAAAG             160

ATGTCAAAGG GACCCAAGAG AGCCTAGCAG AGAAGGAGCT             200

CCAGCTTCTG GTCATGATTC ACCAGCTGTC CACCCTGCGG             240

GACCAGCTCC TGACAGCCCA CTCGGAGCAG AAGAACATGG             280

CTGCCATGCT GTTTGAGAAG CAGCAGCAGC AGATGGAGCT             320

TGCCCGGCAG CAGCAGGAGC AGATTGCAAA GCAGCAGCAG             360

CAGCTGATTC AGCAGCAGCA TAAGATCAAC CTCCTTCAGC             400

AGCAGATCCA GCAGGTTAAC ATGCCTTATG TCATGATCCC             440

AGCCTTCCCC CCAAGCCACC AACCTCTGCC TGTCACCCCT             480

GACTCCCAGC TGGCCTTACC CATTCAGCCC ATTCCCTGCA             520

AACCAGTGGA GTATCCGCTG CAGCTGCTGC ACAGCCCCCC             560

TGCCCCAGTG GTGAAGAGGC TGGGGCATG GCACCCACCA              600

CCCCCTGCAG GAGCCCTCCC AGCCCCTGAA CCTCACAGCC             640

AAGCCCAAGG CCCCCGAGCT GCCCAACACC TCCAGCTCCC             680

CAAGCCTGAA G ATG AGC AGC TGT GTG CCC CGC CCC            715
             Met Ser Ser Cys Val Pro Arg Pro
                                 5
CCC AGC CAT GGA GGC CCC ACG CGG GAC CTG                 745
Pro Ser His Gly Gly Pro Thr Arg Asp Leu
            10                      15

CAG TCC AGC CCC CCG AGC CTG CCT CTG GGC                 775
Gln Ser Ser Pro Pro Ser Leu Pro Leu Gly
            20                      25

TTC CTT GGT GAA GGG GAC GCT GTC ACC AAA                 805
Phe Leu Gly Glu Gly Asp Ala Val Thr Lys
            30                      35

GCC ATC CAG GAT GCT CGG CAG CTG CTG CAC                 835
Ala Ile Gln Asp Ala Arg Gln Leu Leu His
            40                      45

AGC CAC AGT GGG GCC TTG GAT GGC TCC CCC                 865
Ser His Ser Gly Ala Leu Asp Gly Ser Pro
            50                      55

AAC ACC CCC TTC CGT AAG GAC CTC ATC AGC                 895
Asn Thr Pro Phe Arg Lys Asp Leu Ile Ser
            60                      65

CTG GAC TCA TCC CCA GCC AAG GAG CGG CTG                 925
Leu Asp Ser Ser Pro Ala Lys Glu Arg Leu
            70                      75

GAG GAC GGC TGT GTG CAC CCA CTG GAG GAA                 955
Glu Asp Gly Cys Val His Pro Leu Glu Glu
            80                      85

GCC ATG CTG AGC TGC GAC ATG GAT GGC TCC                 985
Ala Met Leu Ser Cys Asp Met Asp Gly Ser
            90                      95

CGC CAC TTC CCC GAG TCC CGA AAC AGC AGC                1015
Arg His Phe Pro Glu Ser Arg Asn Ser Ser
           100                     105

CAC ATC AAG AGG CCC ATG AAC GCC TTC ATG                1045
His Ile Lys Arg Pro Met Asn Ala Phe Met
```

|  |  |
|---|---|
| | 110 115 |
| GTG TGG GCC AAG GAT GAG CGG AGG AAG ATC<br>Val Trp Ala Lys Asp Glu Arg Arg Lys Ile<br>120 125 | 1075 |
| CTG CAA GCC TTC CCA GAC ATG CAC AAC TCC<br>Leu Gln Ala Phe Pro Asp Met His Asn Ser<br>130 135 | 1105 |
| AGC ATC AGC AAG ATC CTT GGA TCT CGC TGG<br>Ser Ile Ser Lys Ile Leu Gly Ser Arg Trp<br>140 145 | 1135 |
| AAG TCC ATG ACC AAC CAG GAG AAG CAG CCC<br>Lys Ser Met Thr Asn Gln Glu Lys Gln Pro<br>150 155 | 1165 |
| TAC TAT GAG GAA CAG GCG CGG CTG AGC CGG<br>Tyr Tyr Glu Glu Gln Ala Arg Leu Ser Lys<br>160 165 | 1195 |
| CAG CAC CTG GAG AAG TAT CCT GAC TAC AAG<br>Gln His Leu Glu Lys Tyr Pro Asp Tyr Lys<br>170 175 | 1225 |
| TAC AAG CCG CGG CCC AAG CGC ACC TGC ATC<br>Tyr Lys Pro Arg Pro Lys Arg Thr Cys Ile<br>180 185 | 1255 |
| GTG GAG GGC AAG CGG CTG CGC GTG GGA GAG<br>Val Glu Gly Lys Arg Leu Arg Val Gly Glu<br>190 195 | 1285 |
| TAC AAG GCC CTG ATG AGG ACC CGG CGT CAG<br>Tyr Lys Ala Leu Met Arg Thr Arg Arg Gln<br>200 205 | 1315 |
| GAT GCC CGC CAG AGC TAC GTG ATC CCC CCG<br>Asp Ala Arg Gln Ser Tyr Val Ile Pro Pro<br>210 215 | 1345 |
| CAG GCT GGC CAG GTG CAG ATG AGC TCC TCA<br>Gln Ala Gly Gln Val Gln Met Ser Ser Ser<br>220 225 | 1375 |
| GAT GTC CTG TAC CCT CGG GCA GCA GGC ATG<br>Asp Val Leu Tyr Pro Arg Ala Ala Gly Met<br>230 235 | 1405 |
| CCG CTG GCA CAG CCA CTG GTG GAG CAC TAT<br>Pro Leu Ala Gln Pro Leu Val Glu His Tyr<br>240 245 | 1435 |
| GTC CCT CGT AGC CTG GAC CCC AAC ATG CCT<br>Val Pro Arg Ser Leu Asp Pro Asn Met Pro<br>250 255 | 1465 |
| GTG ATC GTC AAC ACC TGC AGC CTC AGA GAG<br>Val Ile Val Asn Thr Cys Ser Leu Arg Glu<br>260 265 | 1495 |
| GAG GGT GAG GGC ACA GAT GAC AGG CAC TCG<br>Glu Gly Glu Gly Thr Asp Asp Arg His Ser<br>270 275 | 1525 |
| GTG GCT GAT GGC GAG ATG TAC CGG TAC AGC<br>Val Ala Asp Gly Glu Met Tyr Arg Tyr Ser<br>280 285 | 1555 |
| GAG GAC GAG GAC TCG GAG GGT GAA GAG AAG<br>Glu Asp Glu Asp Ser Glu Gly Glu Glu Lys<br>290 295 | 1585 |
| AGC GAT GGG GAG TTG GTG GTG CTC ACA GAC<br>Ser Asp Gly Glu Leu Val Val Leu Thr Asp<br>300 305 | 1615 |
| TGATCCCGGC TGGGTGGGCC TGGCCCCTTC TCCTCTGGGG | 1655 |

| | |
|---|---|
| AAGACCTTGT CCCAACTCGA TGGGCACAGC CAGCCAACCT | 1695 |
| AAGACTATGT TGGTACTTGG ACTTGTTCGT GCCCCAGAGA | 1735 |
| TGGGCAAAGC TGTGCACTTG CAGATACATT CATGAGGGGA | 1775 |
| GAGGCGCCCT CCCTTCCTGA GGAGCTGTTG GCCTGGGTGG | 1815 |
| GCAGGAACTG CAGTATGGCC ATGGGCTGAG CAGGCTGAGC | 1855 |
| ACCTCAGCCT TTAGGGCTTA TGGCCAGGGG ACACTGTATG | 1895 |
| ACTCTCCTCT CCTGCAGGTG TCTATCCACC TGGGGTATGG | 1935 |
| CATCTACCGA CCTGTCTCCC TGGGGTCACA TGCTTTGTTT | 1975 |
| CCATTCTTGT CCTGGCTGGA CCAGCCACTG TGGGACCAAC | 2015 |
| ACCCCTCCCA CACTCCCCCA GACTGCTCGT CTATCACCAG | 2055 |
| GATCGCTTTG TACTTTGTGC AAAAGGGTCT GGCTGTCCCT | 2095 |
| TGCTGTTTTC ATCTCTGCCA AGCCTATTGT GCCTCTGGCT | 2135 |
| GCTGTATGTG TGCGCGTGCA CGTGTGTGTG TTTCATCTGT | 2175 |
| TCATTCACTG CACAAGATAT TTATTGAGTG CCCACTACGT | 2215 |
| GCCAGGCACT GTTGCTGAGT TCCTGTGGGT GTGTCTCTCG | 2255 |
| ATGCCACTCC TGCTTCTCTG GGGGCCTCTT TCTGTGCTTC | 2295 |
| TCTTTGTCCC CAAATTGCTA CCTCTTTGTC AGTCTGGGTG | 2335 |
| TCTCAGGTTC TGTGTGTCCT TGTGTGCATT TCTGTCTCTC | 2375 |
| TCTGTCCTCG TCTCTCTGCA AGGCCCTCTA TTTCTCTCTT | 2415 |
| TCTTGGTGTC TGTCCTTTGC CCCCTGTGCC CTCTGGATTC | 2455 |
| TCTGGGTCTA TGTAGGCCCC TGGTCTGCCC TGGGCTCATC | 2495 |
| AGCCTTCCTG ACCTCCTCCT GCCCTCCCCT TCACTCCCTC | 2535 |
| CCTGGCTCTG CCAGTCGGTT CCCACGGAGC CATTTTTAGC | 2575 |
| TCTGATCAGC ATGGGAATGT GCCTCGGCCT CCAAGGGGCT | 2615 |
| TTGTCCTGGT GCCCCCGCCC CTGGTCCCAA CCTGATCCCA | 2655 |
| CGAGGGAGTT GGGACAGGAG GATTGATGGT GCTCCCCTTC | 2695 |
| CTGCCAGCGT CAGAGGCCCT GGAGAGGGGC TGTCCATGGC | 2735 |
| AGCTGGTCTT TATTCCTCCC TCATGAGCAC AGGGTCGGGG | 2775 |
| GGGTCCCCAT TCTTGGAAGA GGTTGAGAAG ACTCCTGGGC | 2815 |
| TTCAGCCTCT CCCACCCAGC CCTGCCCCCT CACCTGCCTG | 2855 |
| CCCTCCCCTC CCCCCACTCT ATACTAGGGA CTGGATCTCA | 2895 |
| GCTCTGATCA GTTTCACAAA GTTTGTTCCC TAAGGAAATC | 2935 |
| AAATCCCATT GTCACCTAAC TCTGAAGATC TAAATAGCCC | 2975 |
| TTGGATCAGT ACGGGAACCC CAAATCCCAC AGGGCCAGAT | 3015 |
| GTGGAGTCTG TGTCTGCCCC CGTCTTCTCT CCATCCTCAA | 3055 |
| AGCCCCCACT TCTCTCCAGG CTGTTTCTTT TTTTATGACT | 3095 |
| GTAAACATAG ATAGTGCTTT ATTTTGTTAA TAATAAGATA | 3135 |
| ATGATGAGTA ACTTAACCAG CACATTTCTC CTGTTTACAC | 3175 |
| TCGGGGATT TTTTTGTTTT CTGATGACAT AATAAAGACA | 3215 |

```
GATCATTTCA GAAAAAAAAA AAAAAAAA                                            3243

(2) INFORMATION FOR SEQ ID NO: 7:

(i) SEQUENCE CHARACTERISTICS:
        (A) LENGTH: 2599 nucleotides
        (B) TYPE:   nucleic acid
        (C) STRANDEDNESS: single
        (D) TOPOLOGY: linear (xi) SEQUENCE DESCRIPTION: SEQ ID NO: 7:

GCTGCCTTCA GTCCCTAGTG TCTGGGTCCC CGCCCTCCAG                                40

CCGCCTTTGA GTCGTGCCTG GGTCCTCGCC CTTGCCTCAG                                80

AACCGCGAAG AAAGGAAGCT CGCGTGTTTG CTAGAAAACC                               120

TAGTTGGGAG TGCGAGGCAG AGAACGTTCA GCACCTTTGT                               160

TCCTCCCGAA CCCTCGGGAC AGAGGCAGGG TTCTGAGGGC                               200

AGGGATTCCC CCTCGTCTTG GCCCCACCGC CCGGGCTGGG                               240

CACTAAACTC GGGCCGCGGC GGGGCGAGCG AGGCGGGCTC                               280

CGGAGGGAGC TGACGCCTG ATG ATG GCG CAG TCC                                  314
                    Met Met Ala Gln Ser
                                      5

AAC ATG TTT ACC GTG GCT GAT GTG TTG AGT                                   344
Asn Met Phe Thr Val Ala Asp Val Leu Ser
              10                     15

CAA GAT GAA CTG CGC AAA AAG CTA TAC CAG                                   374
Gln Asp Glu Leu Arg Lys Lys Leu Tyr Gln
              20                     25

ACG TTT AAG GAT CGG GGT ATA CTG GAT ACA                                   404
Thr Phe Lys Asp Arg Gly Ile Leu Asp Thr
              30                     35

CTC AAG ACA CAA CTT CGA AAC CAG CTA ATT                                   434
Leu Lys Thr Gln Leu Arg Asn Gln Leu Ile
              40                     45

CAT GAG TTG ATG CAC CCT GTA TTG AGT GGA                                   464
His Glu Leu Met His Pro Val Leu Ser Gly
              50                     55

GAA CTG CAG CCT CGG TCC ATT TCA GTA GAA                                   494
Glu Leu Gln Pro Arg Ser Ile Ser Val Glu
              60                     65

GGG AGC TCC CTC TTA ATA GGC GCC TCT AAC                                   524
Gly Ser Ser Leu Leu Ile Gly Ala Ser Asn
              70                     75

TCT TTA GTG GCA GAT CAC TTA CAA AGA TGT                                   554
Ser Leu Val Ala Asp His Leu Gln Arg Cys
              80                     85

GGC TAT GAA TAT TCA CTT TCT GTT TTC TTT                                   584
Gly Tyr Glu Tyr Ser Leu Ser Val Phe Phe
              90                     95

CCA GAA AGT GGT TTG GCA AAA GAA AAG GTA                                   614
Pro Glu Ser Gly Leu Ala Lys Glu Lys Val
              100                    105

TTT ACT ATG CAG GAT CTA TTA CAA CTC ATT                                   644
Phe Thr Met Gln Asp Leu Leu Gln Leu Ile
              110                    115

AAA ATC AAC CCT ACT TCC AGT CTC TAC AAA                                   674
Lys Ile Asn Pro Thr Ser Ser Leu Tyr Lys
              120                    125
```

-continued

| | |
|---|---|
| TCA CTG GTT TCA GGA TCT GAT AAA GAA AAT<br>Ser Leu Val Ser Gly Ser Asp Lys Glu Asn<br>130                 135 | 704 |
| CAA AAA GGT TTT CTT ATG CAT TTT TTA AAA<br>Gln Lys Gly Phe Leu Met His Phe Leu Lys<br>140                145 | 734 |
| GAA TTG GCA GAA TAT CAT CAA GCT AAA GAG<br>Glu Leu Ala Glu Tyr His Gln Ala Lys Glu<br>150                155 | 764 |
| AGT TGT AAT ATG GAA ACT CAG ACA AGT TCG<br>Ser Cys Asn Met Glu Thr Gln Thr Ser Ser<br>160                165 | 794 |
| ACA TTT AAC AGA GAT TCT CTG GCT GAG AAG<br>Thr Phe Asn Arg Asp Ser Leu Ala Glu Lys<br>170                175 | 824 |
| CTT CAG CTT ATT GAT GAT CAG TTT GCA GAT<br>Leu Gln Leu Ile Asp Asp Gln Phe Ala Asp<br>180                185 | 854 |
| GCT TAC CCT CAG CGT ATC AAG TTC GAA TCT<br>Ala Tyr Pro Gln Arg Ile Lys Phe Glu Ser<br>190                195 | 884 |
| TTA GAA ATA AAG CTA AAT GTG TAT AAG AGA<br>Leu Glu Ile Lys Leu Asn Val Tyr Lys Arg<br>200                205 | 914 |
| GAA ATA GAA GAG CAA CTT CGG GCA GAA ATG<br>Glu Ile Glu Glu Gln Leu Arg Ala Glu Met<br>210                215 | 944 |
| TGT CAA AAG TTG AAG TTT TTT AAA GAT ACC<br>Cys Gln Lys Leu Lys Phe Phe Lys Asp Thr<br>220                225 | 974 |
| GAG ATA GCA AAA ATT AAA ATG GAA GCA AAA<br>Glu Ile Ala Lys Ile Lys Met Glu Ala Lys<br>230                235 | 1004 |
| AAA AAG TAT GAA AAG GAG TTA ACC ATG TTC<br>Lys Lys Tyr Glu Lys Glu Leu Thr Met Phe<br>240                245 | 1034 |
| CAG AAT GAT TTT GAA AAA GCT TGT CAA GCA<br>Gln Asn Asp Phe Glu Lys Ala Cys Gln Ala<br>250                255 | 1064 |
| AAA TCT GAA GCT CTC GTT CTT CGG GAA AAG<br>Lys Ser Glu Ala Leu Val Leu Arg Glu Lys<br>260                265 | 1094 |
| AGT ACC CTT GAA AGA ATT CAC AAG CAC CAA<br>Ser Thr Leu Glu Arg Ile His Lys His Gln<br>270                275 | 1124 |
| GAG ATT GAA ACA AAA GAA ATT TAT GCT CAA<br>Glu Ile Glu Thr Lys Glu Ile Tyr Ala Gln<br>280                285 | 1154 |
| AGG CAA CTT TTA CTA AAA GAT ATG GAT TTG<br>Arg Gln Leu Leu Leu Lys Asp Met Asp Leu<br>290                295 | 1184 |
| CTA AGA GGA AGA GAA GCA GAG CTG AAG CAA<br>Leu Arg Gly Arg Glu Ala Glu Leu Lys Gln<br>300                305 | 1214 |
| AGA GTT GAA GCT TTT GAA TTG AAC CAG AAG<br>Arg Val Glu Ala Phe Glu Leu Asn Gln Lys<br>310                315 | 1244 |
| CTC CAG GAA GAA AAA CAT AAA AGC ATA ACT<br>Leu Gln Glu Glu Lys His Lys Ser Ile Thr<br>320                325 | 1274 |

```
GAG GCA CTT AGG AGA CAG GAG CAG AAT ATA                                    1304
Glu Ala Leu Arg Arg Gln Glu Gln Asn Ile
            330                 335

AAG AGT TTT GAG GAG ACC TAT GAC CGA AAG                                    1334
Lys Ser Phe Glu Glu Thr Tyr Asp Arg Lys
            340                 345

CTC AAG AAT GAA CTT CTA AAG TAT CAA CTT                                    1364
Leu Lys Asn Glu Leu Leu Lys Tyr Gln Leu
            350                 355

GAA CTG AAG GAT GAC TAC ATC ATT AGA ACT                                    1394
Glu Leu Lys Asp Asp Tyr Ile Ile Arg Thr
            360                 365

AAT CGA CTG ATT GAA GAT GAA AGG AAG AAT                                    1424
Asn Arg Leu Ile Glu Asp Glu Arg Lys Asn
            370                 375

AAA GAA AAA GCT GTT CAT TTG CAA GAG GAG                                    1454
Lys Glu Lys Ala Val His Leu Gln Glu Glu
            380                 385

CTC ATA GCT ATT AAT TCA AAA AAG GAG GAA                                    1484
Leu Ile Ala Ile Asn Ser Lys Lys Glu Glu
            390                 395

CTC AAT CAA TCT GTA AAT CGT GTG AAA GAA                                    1514
Leu Asn Gln Ser Val Asn Arg Val Lys Glu
            400                 405

CTT GAG CTT GAA TTA GAG TCT GTC AAA GCC                                    1544
Leu Glu Leu Glu Leu Glu Ser Val Lys Ala
            410                 415

CAG TCT TTG GCA ATA ACA AAA CAA AAC CAT                                    1574
Gln Ser Leu Ala Ile Thr Lys Gln Asn His
            420                 425

ATG CTG AAT GAA AAG GTT AAA GAG ATG AGT                                    1604
Met Leu Asn Glu Lys Val Lys Glu Met Ser
            430                 435

GAT TAT TCA CTA CTA AAA GAA GAG AAA CTG                                    1634
Asp Tyr Ser Leu Leu Lys Glu Glu Lys Leu
            440                 445

GAG CTT CTG GCA CAA AAT AAA TTA CTT AAA                                    1664
Glu Leu Leu Ala Gln Asn Lys Leu Leu Lys
            450                 455

CAA CAA CTG GAA GAG AGT AGA AAT GAA AAC                                    1694
Gln Gln Leu Glu Glu Ser Arg Asn Glu Asn
            460                 465

CTG CGT CTC CTA AAC CGC CTA GCT CAG CCG                                    1724
Leu Arg Leu Leu Asn Arg Leu Ala Gln Pro
            470                 475

GCT CCT GAA CTT GCA GTC TTT CAG AAA GAA                                    1754
Ala Pro Glu Leu Ala Val Phe Gln Lys Glu
            480                 485

CTA CGG AAA GCC GAA AAG GCT ATA GTG GTT                                    1784
Leu Arg Lys Ala Glu Lys Ala Ile Val Val
            490                 495

GAG CAT GAG GAG TTC GAA AGC TGC AGG CAA                                    1814
Glu His Glu Glu Phe Glu Ser Cys Arg Gln
            500                 505

GCT CTG CAC AAA CAA CTG CAA GAC GAA ATT                                    1844
Ala Leu His Lys Gln Leu Gln Asp Glu Ile
            510                 515

GAG CAT TCT GCA CAG CTG AAG GCC CAG ATT                                    1874
Glu His Ser Ala Gln Leu Lys Ala Gln Ile
```

-continued

```
                  520                 525
CTA GGT TAC AAA GCT TCT GTA AAG AGT TTA                           1904
Leu Gly Tyr Lys Ala Ser Val Lys Ser Leu
                  530                 535

ACT ACT CAG GTT GCC GAT TTA AAA TTG CAA                           1934
Thr Thr Gln Val Ala Asp Leu Lys Leu Gln
                  540                 545

CTG AAG CAA ACT CAG ACA GCC CTA GAG AAT                           1964
Leu Lys Gln Thr Gln Thr Ala Leu Glu Asn
                  550                 555

GAA GTG TAC TGC AAT CCA AAG CAG TCT GTG                           1994
Glu Val Tyr Cys Asn Pro Lys Gln Ser Val
                  560                 565

ATC GAT CGT TCT GTC AAT GGA TTA ATA AAT                           2024
Ile Asp Arg Ser Val Asn Gly Leu Ile Asn
                  570                 575

GGC AAT GTG GTG CCT TGC AAT GGT GAG ATA                           2054
Gly Asn Val Val Pro Cys Asn Gly Glu Ile
                  580                 585

AGT GGG GAT TTC TTG AAC AAT CCT TTT AAA                           2084
Ser Gly Asp Phe Leu Asn Asn Pro Phe Lys
                  590                 595

CAG GAA AAC GTT CTA GCA CGT ATG GTT GCA                           2114
Gln Glu Asn Val Leu Ala Arg Met Val Ala
                  600                 605

TCA AGG ATC ACA AAT TAT CCA ACT GCA TGG                           2144
Ser Arg Ile Thr Asn Tyr Pro Thr Ala Trp
                  610                 615

GTG GAG GGT AGT TCC CCT GAT TCT GAC CTT                           2174
Val Glu Gly Ser Ser Pro Asp Ser Asp Leu
                  620                 625

AAT ACT AAG GCA AGG GTC AAA GAG CTT CAG                           2204
Asn Thr Lys Ala Arg Val Lys Glu Leu Gln
                  630                 635

CAA GAG GCC GAA CGC TTG GAA AAG GCT TTC                           2234
Gln Glu Ala Glu Arg Leu Glu Lys Ala Phe
                  640                 645

AGA AGT TAC CAT CGG AGA GTC ATT AAA AAC                           2264
Arg Ser Tyr His Arg Arg Val Ile Lys Asn
                  650                 655

TCT GCC AAA AGC CCA CTA GCA GCA AAG AGC                           2294
Ser Ala Lys Ser Pro Leu Ala Ala Lys Ser
                  660                 665

CCA CCT CTC TGC ACT TGC TGG AAG CCT TCA                           2324
Pro Pro Leu Cys Thr Cys Trp Lys Pro Ser
                  670                 675

AAA ACA TTA CTT CCA GTT CCC CGG AAA GAC                           2354
Lys Thr Leu Leu Pro Val Pro Arg Lys Asp
                  680                 685

ATA TTT TTG GAG AGG ACA GAG TTG TCT CTG                           2384
Ile Phe Leu Glu Arg Thr Glu Leu Ser Leu
                  690                 695

AGC AGC CTC AAG TGG GCA CAC TTG AAG AAA                           2414
Ser Ser Leu Lys Trp Ala His Leu Lys Lys
                  700                 705

GGA ATG ACG TCG TGG AAG CAC TGACAGGCAG                            2445
Gly Met Thr Ser Trp Lys His
                  710

TGCAGCCTCG AGGCTCCGCG GGGGCACTTC CTCCAGACGC                       2485
```

| | |
|---|---|
| CTCTCTTCCA CACCCCTTCC AAAAGCAAAA AGAAGCCTCG | 2525 |
| AAAGTGAAAT GTATCTGGAA GGTCTGGGCA GATCACACAT | 2565 |
| TGCTTCCCCC AGTCCTTGTC CTGACAGAAT GCCC | 2599 |

(2) INFORMATION FOR SEQ ID NO: 8:

(i) SEQUENCE CHARACTERISTICS:
        (A) LENGTH: 346 nucleotides
        (B) TYPE: nucleic acid
        (C) STRANDEDNESS: single
        (D) TOPOLOGY: linear (xi) SEQUENCE DESCRIPTION: SEQ ID NO: 8:

| | |
|---|---|
| TCGACCTTCG CCTTCAATGG GCTGGCCAGT GGGGGAGAAC | 40 |
| CGGGGAGGTC GGGGAAGAAT CGCTTCCACT CGGAGTGGGG | 80 |
| GGGCGGCTCA CTCCAGGCGA TACAGGCACA GGCAAAGGAG | 120 |
| GGAAGCAAAC AAGGACATAC ATCCTGTGCT CATACAGCCA | 160 |
| TGCACCATGT ATGGGGTTTG TCACATCACT CGTACGCCCC | 200 |
| CACAAGCCTG GAGATAGAAC ATACCTGACT CTAAACCCAA | 240 |
| GACCTCTAAC CACCTTATGG CGCTTTCCTG GGAGACCCAA | 280 |
| TGAGGGAATG ACATTTAAAG CCCTCCCTAG ACCAGAGTTC | 320 |
| TCAGGGTACT TTTCTATTAA AAAAAA | 346 |

(2) INFORMATION FOR SEQ ID NO: 9:

(i) SEQUENCE CHARACTERISTICS:
        (A) LENGTH: 1413 nucleotides
        (B) TYPE: nucleic acid
        (C) STRANDEDNESS: single
        (D) TOPOLOGY: linear (xi) SEQUENCE DESCRIPTION: SEQ ID NO: 9:

```
TC AAC CGG GCA GAG GGT CCA CCG GAG CCT TCA              32
   Asn Arg Ala Glu Gly Pro Pro Glu Pro Ser
                    5                   10

CGG GTG AGC AGT GTG TCC TCC CAG TTC AGC                 62
Arg Val Ser Ser Val Ser Ser Gln Phe Ser
             15                      20

GAC GCA GCC CAG GCC AGC CCC AGC TCC CAC                 92
Asp Ala Ala Gln Ala Ser Pro Ser Ser His
             25                      30

AGC AGC ACC CCG TCC TGG TGC GAG GAG CCG                122
Ser Ser Thr Pro Ser Trp Cys Glu Glu Pro
             35                      40

GCC CAA GCC AAC ATG GAC ATC TCC ACG GGA                152
Ala Gln Ala Asn Met Asp Ile Ser Thr Gly
             45                      50

CAC ATG ATT CTG GCA TAC ATG GAG GAT CAC                182
His Met Ile Leu Ala Tyr Met Glu Asp His
             55                      60

CTG CGG AAC CGG GAC CGC CTT GCC AAG GAG                212
Leu Arg Asn Arg Asp Arg Leu Ala Lys Glu
             65                      70

TGG CAG GCC CTC TGT GCC TAC CAA GCA GAG                242
Trp Gln Ala Leu Cys Ala Tyr Gln Ala Glu
             75                      80

CCA AAC ACC TGT GCC ACC GCG CAG GGG GAG                272
```

```
Pro Asn Thr Cys Ala Thr Ala Gln Gly Glu
             85                  90

GGC AAC ATC AAA AAG AAC CGG CAT CCT GAC                          302
Gly Asn Ile Lys Lys Asn Arg His Pro Asp
             95                 100

TTC CTG CCC TAT GAC CAT GCC CGC ATA AAA                          332
Phe Leu Pro Tyr Asp His Ala Arg Ile Lys
            105                 110

CTG AAG GTG GAG AGC AGC CCT TCT CGG AGC                          362
Leu Lys Val Glu Ser Ser Pro Ser Arg Ser
            115                 120

GAT TAC ATC AAC GCC AGC CCC ATT ATT GAG                          392
Asp Tyr Ile Asn Ala Ser Pro Ile Ile Glu
            125                 130

CAT GAC CCT CGG ATG CCA GCC TAC ATA GCC                          422
His Asp Pro Arg Met Pro Ala Tyr Ile Ala
            135                 140

ACG CAG GGC CCG CTG TCC CAT ACC ATC GCA                          452
Thr Gln Gly Pro Leu Ser His Thr Ile Ala
            145                 150

GAC TTC TGG CAG ATG GTG TGG GAG AGC GGC                          482
Asp Phe Trp Gln Met Val Trp Glu Ser Gly
            155                 160

TGC ACC GTC ATC GTC ATG CTG ACC CCG CTG                          512
Cys Thr Val Ile Val Met Leu Thr Pro Leu
            165                 170

GTG GAG GAT GGT GTC AAG CAG TGT GAC CGC                          542
Val Glu Asp Gly Val Lys Gln Cys Asp Arg
            175                 180

TAC TGG CCA GAT GAG GGT GCC TCC CTC TAC                          572
Tyr Trp Pro Asp Glu Gly Ala Ser Leu Tyr
            185                 190

CAC GTA TAT GAG GTG AAC CTG GTG TCG GAG                          602
His Val Tyr Glu Val Asn Leu Val Ser Glu
            195                 200

CAC ATC TGG TGC GAG GAC TTT CTG GTG CGG                          632
His Ile Trp Cys Glu Asp Phe Leu Val Arg
            205                 210

AGC TTC TAC CTG AAG AAC GTG CAG ACC CAG                          662
Ser Phe Tyr Leu Lys Asn Val Gln Thr Gln
            215                 220

GAG ACG CGC ACG CTC ACG CAG TTC CAC TTC                          692
Glu Thr Arg Thr Leu Thr Gln Phe His Phe
            225                 230

CTC AGC TGG CCG GCA GAG GGC ACA CCG GCC                          722
Leu Ser Trp Pro Ala Glu Gly Thr Pro Ala
            235                 240

TCC ACG CGG CCC CTG CTG GAC TTC CGC AGG                          752
Ser Thr Arg Pro Leu Leu Asp Phe Arg Arg
            245                 250

AAG GTG AAC AAG TGC TAC CGG GGC CGC TCC                          782
Lys Val Asn Lys Cys Tyr Arg Gly Arg Ser
            255                 260

TGC CCC ATC ATC GTG CAC TGC AGT GAT GGT                          812
Cys Pro Ile Ile Val His Cys Ser Asp Gly
            265                 270

GCG GGG AGG ACC GGC ACC TAC ATC CTC ATC                          842
Ala Gly Arg Thr Gly Thr Tyr Ile Leu Ile
            275                 280
```

| | |
|---|---|
| GAC ATG GTC CTG AAC CGC ATG GCA AAA GGA<br>Asp Met Val Leu Asn Arg Met Ala Lys Gly<br>               285                   290 | 872 |
| GTG AAG GAG ATT GACATCGCT GCCACCCTGGA<br>Val Lys Glu Ile | 904 |
| GCATGTCCGT GACCAGCGGC CTGGCCTTGT CCGCTCTAAG | 944 |
| GACCAGTTTG AATTTGCCCT GACAGCCGTG GCGGAGGAAG | 984 |
| TGAATGCCAT CCTCAAGGCC CTGCCCCAGT GAGACCCTGG | 1024 |
| GGCCCCTTGG CGGGCAGCCC AGCCTCTGTC CCTCTTTGCC | 1064 |
| TGTGTGAGCA TCTCTGTGTA CCCACTCCTC ACTGCCCCAC | 1104 |
| CAGCCACCTC TTGGGCATGC TCAGCCCTTC CTAGAAGAGT | 1144 |
| CAGGAAGGGA AAGCCAGAAG GGGCACGCCT GCCCAGCCTC | 1184 |
| GCATGCCAGA GCCTGGGGCA TCCCAGAGCC CAGAGCATCC | 1224 |
| CATGGGGGTG CTGCAGCCAG GAGGAGAGGA AAGGACATGG | 1264 |
| GTAGCAATTC TACCCAGAGC CTTCTCCTGC CTACATTCCC | 1304 |
| TGGCCTGGCT CTCCTGTAGC TCTCCTGGGG TTCTGGGAGT | 1344 |
| TCCCTGAACA TCTGTGTGTG TCCCCCTATG CTCCAGTATG | 1384 |
| GAAGAATGGG GTGGAGGGTC GCCACACCC | 1413 |

(2) INFORMATION FOR SEQ ID NO: 10:

(i) SEQUENCE CHARACTERISTICS:
        (A) LENGTH: 3311 nucleotides
        (B) TYPE: nucleic acid
        (C) STRANDEDNESS: single
        (D) TOPOLOGY: linear (xi) SEQUENCE DESCRIPTION: SEQ ID NO: 10:

| | |
|---|---|
| CTCCAACGCT TACAAGGTGT GCTCCGACAA CTCATGTCCC | 40 |
| AAGGATTGTC CTGGCACGAT GACCTCACCC AGTATGTGAT | 80 |
| CTCTCAGGAG ATGGAGCGCA TCCCCAGGCT TCGCCCCCCA | 120 |
| GAGCCCCGTC CAAGGGACAG GTCTGGCTTG GCACCCAAGA | 160 |
| GACCTGGTCC TGCTGGAGAG CTGCTTTTAC AGGACATCCC | 200 |
| CACTGGCTCC GCCCCTGCTG CCCAGCATCG GCTTCCACAA | 240 |
| CCACCAGTGG GCAAAGGTGG AGCTGGGGCC AGCTCCTCTC | 280 |
| TGTCCCCTCT GCAGGCTGAG CTGCTCCCGC CTCTCTTGGA | 320 |
| GCACCTGCTG CTGCCCCCAC AGCCTCCCCA CCCTTCACTG | 360 |
| AGTTACGAAC CTGCCTTGCT GCAGCCCTAC CTGTTCCACC | 400 |
| AGTTTGGCTC CCGTGATGGC TCCAGGGTCT CAGAGGGCTC | 440 |
| CCCAGGGATG GTCAGTGTCG GCCCCCTGCC CAAGGCTGAA | 480 |
| GCCCCTGCCC TCTTCAGCAG AACTGCCTCC AAGGGCATAT | 520 |
| TTGGGGACCA CCCTGGCCAC TCCTACGGGG ACCTTCCAGG | 560 |
| GCCTTCACCT GCCCAGCTTT TTCAAGACTC TGGGCTGCTC | 600 |
| TATCTGGCCC AGGAGTTGCC AGCACCCAGC AGGGCCAGGG | 640 |
| TGCCAAGGCT GCCAGAGCAA GGGAGCAGCA GCCGGGCAGA | 680 |
| GGACTCCCCA GAGGGCTATG AGAAGGAAGG ACTAGGGGAT | 720 |

-continued

```
CGTGGAGAGA AGCCTGCTTC CCCAGCTGTG CAGCCAGATG                760

CGGCTCTGCA GAGGCTGGCC GCTGTGCTGG CGGGCTATGG                800

GGTAGAGCTG CGTCAGCTGA CCCCTGAGCA GCTCTCCACA                840

CTCCTGACCC TGCTGCAGCT ACTGCCCAAG GGTGCAGGAA                880

GAAATCCGGG AGGGGTTGTA AATGTTGGAG CTGATATCAA                920

GAAAACA ATG GAG GGG CCG GTG GAG GGC                        948
        Met Glu Gly Pro Val Glu Gly
          1           5

AGA GAC ACA GCA GAG CTT CCA GCC CGC ACA                    978
Arg Asp Thr Ala Glu Leu Pro Ala Arg Thr
 10              15

TCC CCC ATG CCT GGA CAC CCC ACT GCC AGC                    1008
Ser Pro Met Pro Gly His Pro Thr Ala Ser
 20              25

CCT ACC TCC AGT GAA GTC CAG CAG GTG CCA                    1038
Pro Thr Ser Ser Glu Val Gln Gln Val Pro
 30              35

AGC CCT GTC TCC TCT GAG CCT CCC AAA GCT                    1068
Ser Pro Val Ser Ser Glu Pro Pro Lys Ala
 40              45

GCC AGA CCC CCT GTG ACA CCT GTC CTG CTA                    1098
Ala Arg Pro Pro Val Thr Pro Val Leu Leu
 50              55

GAG AAG AAA AGC CCA CTG GGC CAG AGC CAG                    1128
Glu Lys Lys Ser Pro Leu Gly Gln Ser Gln
 60              65

CCC ACG GTG GCA GGA CAG CCC TCA GCC CGC                    1158
Pro Thr Val Ala Gly Gln Pro Ser Ala Arg
 70              75

CCA GCA GCA GAG GAA TAT GGC TAC ATC GTC                    1188
Pro Ala Ala Glu Glu Tyr Gly Tyr Ile Val
 80              85

ACT GAT CAG AAG CCC CTG AGC CTG GCT GCA                    1218
Thr Asp Gln Lys Pro Leu Ser Leu Ala Ala
 90              95

GGA GTG AAG CTG CTG GAG ATC CTG GCT GAG                    1248
Gly Val Lys Leu Leu Glu Ile Leu Ala Glu
100             105

CAT GTG CAC ATG TCC TCA GGC AGC TTC ATC                    1278
His Val His Met Ser Ser Gly Ser Phe Ile
110             115

AAC ATC AGT GTG GTG GGA CCA GCC CTC ACC                    1308
Asn Ile Ser Val Val Gly Pro Ala Leu Thr
120             125

TTC CGC ATC CGG CAC AAT GAG CAG AAC CTG                    1338
Phe Arg Ile Arg His Asn Glu Gln asn Leu
130             135

TCT TTG GCT GAT GTG ACC CAA CAA GCA GGG                    1368
Ser Leu Ala Asp Val Thr Gln Gln Ala Gly
140             145

CTG GTG AAG TCT GAA CTG GAA GCA CAG ACA                    1398
Leu Val Lys Ser Glu Leu Glu Ala Gln Thr
150             155

GGG CTC CAA ATC TTG CAG ACA GGA GTG GGA                    1428
Gly Leu Gln Ile Leu Gln Thr Gly Val Gly
160             165
```

| | |
|---|---|
| CAG AGG GAG GAG GCA GCT GCA GTC CTT CCC<br>Gln Arg Glu Glu Ala Ala Ala Val Leu Pro<br>170                      175 | 1458 |
| CAA ACT GCG CAC AGC ACC TCA CCC ATG CGC<br>Gln Thr Ala His Ser Thr Ser Pro Met Arg<br>180                      185 | 1488 |
| TCA GTG CTG CTC ACT CTG GTG GCC CTG GCA<br>Ser Val Leu Leu Thr Leu Val Ala Leu Ala<br>190                      195 | 1518 |
| GGT GTG GCT GGG CTG CTG GTG GCT CTG GCT<br>Gly Val Ala Gly Leu Leu Val Ala Leu Ala<br>200                      205 | 1548 |
| GTG GCT CTG TGT GTG CGG CAG CAT GCG CGG<br>Val Ala Leu Cys Val Arg Gln His Ala Arg<br>210                      215 | 1578 |
| CAG CAA GAC AAG GAG CGC CTG GCA GCC CTG<br>Gln Gln Asp Lys Glu Arg Leu Ala Ala Leu<br>220                      225 | 1608 |
| GGG CCT GAG GGG GCC CAT GGT GAC ACT ACC<br>Gly Pro Glu Gly Ala His Gly Asp Thr Thr<br>230                      235 | 1638 |
| TTT GAG TAC CAG GAC CTG TGC CGC CAG CAC<br>Phe Glu Tyr Gln Asp Leu Cys Arg Gln His<br>240                      245 | 1668 |
| ATG GCC ACG AAG TCC TTG TTC AAC CGG GCA<br>Met Ala Thr Lys Ser Leu Phe Asn Arg Ala<br>250                      255 | 1698 |
| GAG GGT CCA CCG GAG CCT TCA CGG GTG AGC<br>Glu Gly Pro Pro Glu Pro Ser Arg Val Ser<br>260                      265 | 1728 |
| AGT GTG TCC TCC CAG TTC AGC GAC GCA GCC<br>Ser Val Ser Ser Gln Phe Ser Asp Ala Ala<br>270                      275 | 1758 |
| CAG GCC AGC CCC AGC TCC CAC AGC AGC ACC<br>Gln Ala Ser Pro Ser Ser His Ser Ser Thr<br>280                      285 | 1788 |
| CCG TCC TGG TGC GAG GAG CCG GCC CAA GCC<br>Pro Ser Trp Cys Glu Glu Pro Ala Gln Ala<br>290                      295 | 1818 |
| AAC ATG GAC ATC TCC ACG GGA CAC ATG ATT<br>Asn Met Asp Ile Ser Thr Gly His Met Ile<br>300                      305 | 1848 |
| CTG GCA TAC ATG GAG GAT CAC CTG CGG AAC<br>Leu Ala Tyr Met Glu Asp His Leu Arg Asn<br>310                      315 | 1878 |
| CGG GAC CGC CTT GCC AAG GAG TGG CAG GCC<br>Arg Asp Arg Leu Ala Lys Glu Trp Gln Ala<br>320                      325 | 1908 |
| CTC TGT GCC TAC CAA GCA GAG CCA AAC ACC<br>Leu Cys Ala Tyr Gln Ala Glu Pro Asn Thr<br>330                      335 | 1938 |
| TGT GCC ACC GCG CAG GGG GAG GGC AAC ATC<br>Cys Ala Thr Ala Gln Gly Glu Gly Asn Ile<br>340                      345 | 1968 |
| AAA AAG AAC CGG CAT CCT GAC TTC CTG CCC<br>Lys Lys Asn Arg His Pro Asp Phe Leu Pro<br>350                      355 | 1998 |
| TAT GAC CAT GCC CGC ATA AAA CTG AAG GTG<br>Tyr Asp His Ala Arg Ile Lys Leu Lys Val<br>360                      365 | 2028 |

```
GAG AGC AGC CCT TCT CGG AGC GAT TAC ATC                    2058
Glu Ser Ser Pro Ser Arg Ser Asp Tyr Ile
370                 375

AAC GCC AGC CCC ATT ATT GAG CAT GAC CCT                    2088
Asn Ala Ser Pro Ile Ile Glu His Asp Pro
380                 385

CGG ATG CCA GCC TAC ATA GCC ACG CAG GGC                    2118
Arg Met Pro Ala Tyr Ile Ala Thr Gln Gly
390                 395

CCG CTG TCC CAT ACC ATC GCA GAC TTC TGG                    2148
Pro Leu Ser His Thr Ile Ala Asp Phe Trp
400                 405

CAG ATG GTG TGG GAG AGC GGC TGC ACC GTC                    2178
Gln Met Val Trp Glu Ser Gly Cys Thr Val
410                 415

ATC GTC ATG CTG ACC CCG CTG GTG GAG GAT                    2208
Ile Val Met Leu Thr Pro Leu Val Glu Asp
420                 425

GGT GTC AAG CAG TGT GAC CGC TAC TGG CCA                    2238
Gly Val Lys Gln Cys Asp Arg Tyr Trp Pro
430                 435

GAT GAG GGT GCC TCC CTC TAC CAC GTA TAT                    2268
Asp Glu Gly Ala Ser Leu Tyr His Val Tyr
440                 445

GAG GTG AAC CTG GTG TCG GAG CAC ATC TGG                    2298
Glu Val Asn Leu Val Ser Glu His Ile Trp
450                 455

TGC GAG GAC TTT CTG GTG CGG AGC TTC TAC                    2328
Cys Glu Asp Phe Leu Val Arg Ser Phe Tyr
460                 465

CTG AAG AAC GTG CAG ACC CAG GAG ACG CGC                    2358
Leu Lys Asn Val Gln Thr Gln Glu Thr Arg
470                 475

ACG CTC ACG CAG TTC CAC TTC CTC AGC TGG                    2388
Thr Leu Thr Gln Phe His Phe Leu Ser Trp
480                 485

CCG GCA GAG GGC ACA CCG GCC TCC ACG CGG                    2418
Pro Ala Glu Gly Thr Pro Ala Ser Thr Arg
490                 495

CCC CTG CTG GAC TTC CGC AGG AAG GTG AAC                    2448
Pro Leu Leu Asp Phe Arg Arg Lys Val Asn
500                 505

AAG TGC TAC CGG GGC CGC TCC TGC CCC ATC                    2478
Lys Cys Tyr Arg Gly Arg Ser Cys Pro Ile
510                 515

ATC GTG CAC TGC AGT GAT GGT GCG GGG AGG                    2508
Ile Val His Cys Ser Asp Gly Ala Gly Arg
520                 525

ACC GGC ACC TAC ATC CTC ATC GAC ATG GTC                    2538
Thr Gly Thr Tyr Ile Leu Ile Asp Met Val
530                 535

CTG AAC CGC ATG GCA AAA GGA GTG AAG GAG                    2568
Leu Asn Arg Met Ala Lys Gly Val Lys Glu
540                 545

ATT GACATCGCTG CCACCCTGGA GCATGTCCGT                       2601
Ile

GACCAGCGGC CTGGCCTTGT CCGCTCTAAG GACCAGTTTG                2641

AATTTGCCCT GACAGCCGTG GCGGAGGAAG TGAATGCCAT                2681
```

```
CCTCAAGGCC CTGCCCCAGT GAGACCCTGG GGCCCCTTGG                    2721

CGGGCAGCCC AGCCTCTGTC CCTCTTTGCC TGTGTGAGCA                    2761

TCTCTGTGTA CCCACTCCTC ACTGCCCCAC CAGCCACCTC                    2801

TTGGGCATGC TCAGCCCTTC CTAGAAGAGT CAGGAAGGGA                    2841

AAGCCAGAAG GGGCACGCCT GCCCAGCCTC GCATGCCAGA                    2881

GCCTGGGGCA TCCCAGAGCC CAGAGCATCC CATGGGGTG                     2921

CTGCAGCCAG GAGGAGAGGA AAGGACATGG GTAGCAATTC                    2961

TACCCAGAGC CTTCTCCTGC CTACATTCCC TGGCCTGGCT                    3001

CTCCTGTAGC TCTCCTGGGG TTCTGGGAGT TCCCTGAACA                    3041

TCTGTGTGTG TCCCCCTATG CTCCAGTATG GAAGAATGGG                    3081

GTGGAGGGTC GCCACACCCG GCTCCCCCTG CTTCTCAGCC                    3121

CCGGGCCTGC CTCTGACTCA CACTTGGGCG CTCTGCCCTC                    3161

CCTGGCCTCA CGCCCAGCCT CCTCCCACCA CCCTCCCACC                    3201

ATGCGCTGCT CAACCTCTCT CCTTCTGGCG CAAGAGAACA                    3241

TTTCTAGAAA AAACTACTTT TGTACCAGTG TGAATAAAGT                    3281

TAGTGTGTTG TCTGTGCAGC TGCAAAAAAA                               3311
```